United States Patent [19]

Frehel et al.

[11] Patent Number: 5,189,049

[45] Date of Patent: Feb. 23, 1993

[54] HETEROCYCLIC SUBSTITUTED ACYLAMINOTHIAZOLES, THEIR PREPARATION AND PHARMACEUTICAL COMPOSITIONS CONTAINING THEM

[75] Inventors: Daniel Frehel, Toulouse; Danielle Gully, Muret; Gerard Valette, Lacroix; Jean-Pierre Bras, Toulouse, all of France

[73] Assignee: Sanofi, Paris, France

[21] Appl. No.: 622,620

[22] Filed: Dec. 5, 1990

[30] Foreign Application Priority Data

Dec. 6, 1989 [FR] France .................. 89 16122
May 4, 1990 [FR] France .................. 90 05669

[51] Int. Cl.$^5$ .................. A07D 417/12; A61K 31/425
[52] U.S. Cl. .................. 514/371; 514/301; 514/307; 514/314; 546/114; 546/146; 546/169; 548/150; 548/181; 548/195
[58] Field of Search .................. 548/181, 150, 195; 546/114, 146, 169; 514/331, 306, 301, 307, 314

[56] References Cited

FOREIGN PATENT DOCUMENTS

| 40573 | 11/1981 | European Pat. Off. .......... 546/156 |
| 0208510 | 1/1987 | European Pat. Off. . |
| 0308885 | 3/1989 | European Pat. Off. . |
| 0348523 | 1/1990 | European Pat. Off. . |
| 0356234 | 2/1990 | European Pat. Off. . |
| 3705934 | 9/1988 | Fed. Rep. of Germany . |
| 2340092 | 9/1977 | France . . |
| 8905812 | 6/1989 | World Int. Prop. O. . |

OTHER PUBLICATIONS

Chemical Abstracts 67 100049z 100051u (1967).

Primary Examiner—Robert Gerstl

Attorney, Agent, or Firm—Wegner, Cantor, Mueller & Player

[57] ABSTRACT

Compounds of formula

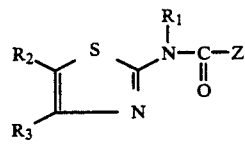

in which $R_1$ represents H, an alkyl or a substituted alkyl, $R_2$ represents H or alkyl and $R_3$ represents an optionally substituted cycloalkyl or an optionally substituted aromatic group, which can be a phenyl or a heterocyclic group comprising one or more hetero-atoms chosen from O, S and N, or $R_2$ and $R_3$ considered together represent the group

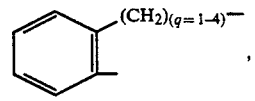

which is optionally substituted on the phenyl ring, and Z represents a heterocycle comprising one or more heteroatoms chosen from O, S and N, fused with an aromatic ring which can comprise a hetero-atom and can be substituted, the said heterocycle being optionally substituted on N, when it comprises such an atom, by an alkyl or a substituted alkyl group, and the salts of these compounds with acids or bases.

Use of these compounds as medicaments.

No figure.

15 Claims, No Drawings

HETEROCYCLIC SUBSTITUTED ACYLAMINOTHIAZOLES, THEIR PREPARATION AND PHARMACEUTICAL COMPOSITIONS CONTAINING THEM

The present invention relates to heterocyclic compounds which are cholecystokinin and gastrin antagonists.

Cholecystokinin (CCK) is a polypeptide hormone present in vivo in various forms comprising from 8 t 39 amino acids. It has numerous physiological activities on the bile ducts, the gastrointestinal tract and on the central and peripheral nervous systems and reference can be made to the article by J. E. Morley in Life Sciences vol. 30, p. 479-493 (1982), which gives a detailed review of its properties. Two different types of CCK receptors have been demonstrated with the use of specific antagonists; those of type A present in particular in the pancrease, the glass bladder and some area of the central nervous system, while those of type B are found above all in the central nervous system.

Gastrin is a polypeptide hormone which acts in particular on the acid secretion of the stomach; its 5 C-terminal amino acids are identical to those of CCK.

Gastrin and/or CCK antagonist compounds have already been described, in particular proglumide and p-chlorobenzoyl-L-tryptophane, or, more recently, benzodiazepin derivatives which are specific antagonists either of CCK A receptors, such as 3S(−)-N-[1-methyl-2-oxo-5-phenyl-2,3-dihydro-1H-1,4-benzodiazepin-3-yl]-indole-2-carboxamide (cf. Eur. J. Pharmacology 162, 273–280, (1989)) or of CCK B receptors, such as 3R(+)-N-[1-methyl-2-oxo-5-phenyl-2,3-dihydro-1H-1,4-benzodiazepin-3-yl]-N'-[3-methylphenyl]urea.

The compounds according to the invention are heterocyclic unsubstituted 2-acylaminothiazoles of formula I:

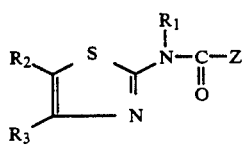

in which $R_1$ represents a hydrogen atom, a ($C_1$ to $C_4$) alkyl group or a phenylalkyl group containing ($C_1$ to $C_3$) alkyl; an amino alkyl group of formula $-Z_1-NR_4R_5$, in which $Z_1$ represents a ($C_2$ to $C_4$) alkylene and $R_4$ and $R_5$ independently represent H or a ($C_1$ to $C_4$) alkyl or form, with the nitrogen atom to which they are bonded, a saturated heterocycle such as morpholino, pyrrolidinyl, piperidino, piperazinyl or 4-($C_1$-$C_3$)alkylpiperazinyl; an optionally esterified carboxyalkyl group of formula $-Z_2-COOR_6$, in which $Z_2$ represents a ($C_1$ to $C_4$) alkylene and $R_6$ represents H or a ($C_1$ to $C_6$) alkyl; a ($C_2$ to $C_5$) cyanoalkyl group; a carbamoylalkyl group of formula $-Z_3-CONR_7R_8$, in which $Z_3$ represents a ($C_1$ to $C_4$) alkylene and $R_7$ and $R_6$ independently represent H or a ($C_1$ to $C_4$) alkyl or, with N, represent a heterocycle such as $NR_4R_5$; a ($C_2$ to $C_6$) hydroxyalkyl group or a ($C_2$ to $C_{10}$) alkoxyalkyl group, $R_2$ represents a hydrogen atom or a ($C_1$ to $C_4$) alkyl group; $R_3$ represents a ($C_5$ to $C_8$) cycloalkyl group which is optionally substituted by one or more ($C_1$ to $C_4$) alkyl groups; an aromatic group, such as a phenyl, optionally carrying one of more substituents chosen from halogen atoms, in particular chlorine or fluorine, ($C_1$-$C_6$) alkyl and ($C_1$ to $C_3$) alkoxy and thioalkoxy groups and nitro and trifluoromethyl groups, or such as a heterocycle comprising at least one hetero-atom chosen from O, S, and N, in particular furyl, thienyl, pyrrolyl, pyrazolyl, imidazolyl, pyridyl, pyrazinyl, oxazolyl and thiazolyl, which are optionally substituted by a ($C_1$ to $C_3$) alkyl group or a halogen atom, or $R_2$ and $R_3$ considered together represent the group

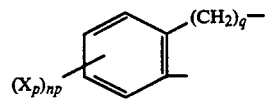

fixed by the carbon of the phenyl in position 4 of the thiazolyl ring and in which q is 1to 4, optionally carrying one or more (np) substituents Xp, which may be identical or different and are chosen from halogen atoms, ($C_1$ to $C_3$) alkyl and alkoxy groups and the nitro and trifluoromethyl groups, np being from 0 to 3, and Z represents a heterocycle comprising one or more heteroatoms chosen from O, S and N, fused with an aromatic ring which may also comprise a hetero-atom chosen from O, S and N and which may be substituted by one or more groups chosen from halogen atoms, ($C_1$ to $C_3$) alkyl and alkoxy, benzyloxy, nitro, amino and trifluoromethyl groups, as well as the addition salts of these compounds with inorganic or organic acids and bases; the pharmaceutically acceptable non-toxic salts are preferred, but other salts which can be used to isolate or purify the compounds of formula I are also within the invention.

The alkyl, alkylene, alkoxy and thioalkoxy groups can be straight-chain or branched.

Z represents in particular benzothienyl, benzofuranyl, benzoxazolyl, benzimidazoly, benzothiazolyl, indolyl, isoindolyl, indolinyl, isoindolinyl, quinolyl, isoquinolyl, quinoxalinyl, quinazolinyl, cinnolinyl and [2,3-c] or [3,2-c]thienopyridyl groups.

When Z represents an indolyl or indolinyl group of formula

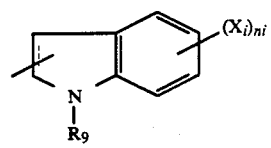

in which $(X_i)_{ni}$ represents the optional substituents on the aromatic ring, $R_9$ may represent H; a ($C_1$ to $C_4$) alkyl group; a ($C_1$ to $C_6$) hydroxyalkyl group; an optionally cyclised ($C_2$ to $C_{10}$) alkoxyalkyl group, such as a tetrahydropyranyl; an amino alkyl group of formula $-Z_4-NR_{10}R_{11}$, in which $Z_4$ represents a ($C_2$ to $C_4$) alkylene and $R_{10}$ and $R_{11}$ independently represent H or a ($C_1$ to $C_4$) alkyl or form, with the nitrogen atom to which they are bonded, a saturated heterocyclic group such as morpholino, pyrrolidinyl, piperidino, piperazinyl or 4-($C_1$-$C_3$)alkylpiperazinyl; an optionally esterified carboxyalkyl group of formula $-Z_5-COOR_{12}$ in which $Z_5$ represents a ($C_1$ to $C_4$) alkylene and $R_{12}$ represents H, benzyl or a ($C_1$ to $C_6$) alkyl; a cyanoalkyl group containing ($C_1$ to $C_4$) alkyl; a carbamoylalkyl group of formula $-Z_6-CONR_{13}R_{14}$ in which $R_{13}$ and $R_{14}$ independently represent H or a ($C_1$ to $C_6$) alkyl or form, with N, a saturated heterocycle such as $NR_{10}R_{11}$, and $Z_6$ is a ($C_1$ to $C_4$) alkylene; an acyl group of formula $COR_{15}$, in which $R_{15}$ represents a ($C_1$ to $C_4$) alkyl or phenyl; or an alkoxycarbonyl group of formula $COOR_{16}$, in which $R_{16}$ represents t-butyl or benzyl.

Amongst the compounds of formula I, those in which $R_1$ represents H, an alkyl or an amino alkyl are preferred, and amongst these, those in which Z represents an indolyl group which is unsubstituted or substituted on the nitrogen are more particularly preferred; amongst the groups $R_3$, the preferred groups are phenyl which are at least ortho-substituted, when $R_2$ represents H.

The compounds of formula I may be prepared by a coupling reaction of an aminothiazole of formula II

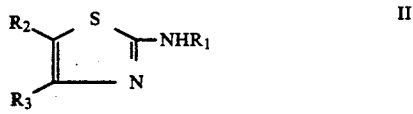

under the usual conditions for acylation of an amine, with an acid of formula Z'COOH, in which Z' represents Z or a derivative of Z in which the reactive groups of Z have been protected, and $R_1$, $R_2$, $R_3$ and Z have the same meaning as in the formula I, or with an activated form of the acid Z'COOH, such as an acid halide, an acid anhydride, and preferably a mixed anhydride such as a carbonic anhydride, or an activated ester, obtained using the reagents commonly used in peptide synthesis.

The compounds of formula I in which Z is replaced by Z' are also within the invention as synthetic intermediates; furthermore, some have, in vivo, the same therapeutic activity, in particular owing to their metabolisation to compounds of formula I.

When groups have been protected, the appropriate deprotection reaction is carried out, if necessary, after the condensation reaction.

Numerous aminothiazoles of formula II are known.

The new aminothiazoles may be prepared in accordance with one of the processes described previously, in particular in Bull. Soc. Chim. (C) p. 2498–2503 (1963).

In general, a thiourea will be reacted with an alpha-halogenated, and preferably alpha-brominated, ketone, in accordance with the reaction scheme:

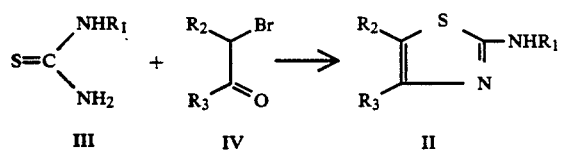

$R_1$, $R_2$ and $R_3$ having the same meaning as in the formula II.

The preparation of various compounds II in which $R_1$ represents an aminoalkyl group is described in EP-A-0,283,390.

The alpha-halogenated ketones and the thioureas can be prepared by processes for which the principles are described in the literature; thus, the alpha-brominated ketones (IV) may be prepared by the action of bromine on $R_2CH_2COR_3$ in an acetic acid medium, or of cupric bromide on $R_2CH_2COR_3$ in an organic solvent such as ethyl acetate, a chlorinated solvent or their mixtures. The starting aromatic ketones are generally prepared by a Friedel-Crafts reaction, while the aliphatic methyl ketones can be prepared by the action of diazomethane on the appropriate carboxylic acid chlorides, followed by hydrolysis of the corresponding diazoketone.

The alpha-chlorinated aromatic ketones may be prepared by a Friedel-Crafts reaction using the appropriate alpha-chlorinated acid chlorides, or by chloroacetylation using N,N-dimethylchloroacetamide when $R_2$=H.

The substituted thoureas III of formula $H_2NCSNHCH_2COOR_6$ are prepared by esterification of commercial acid, and those of formula $H_2NCSNHCH_2CONR_4R_5$ by converting the acid to the amide; the others may be prepared by the action of the amine $R_1NH_2$ on $(CH_3)_3C$—CO—N=C=S or on $C_6H_5$—CO—N=C=S.

These latter compounds are obtained, respectively, by the action of pivaloyl or benzoyl chloride on potassium thiocyanate in an anhydrous inert solvent, such as a ketone; the coupling reaction with the amine $R_1NH_2$ may be carried out without isolating the acyl isothiocyanate. When $R_1$ comprises an alkoxycarbonyl group, it is preferred to use the pivaloyl derivative to effect the hydrolysis of the acylthiourea intermediate in an anhydrous strong acid medium, without the hydrolysis of the alkoxycarbonyl group; the hydrolysis of benzoylthiourea is generally carried out by reacting an aqueous solution of an inorganic base, such as NaOH.

Some of the acids ZCOOH, or Z'COOH, are known and even available commercially; the others are prepared using the methods known for analogous molecules.

Thus, the indolecarboxylic acids, of formula Z"COOH:

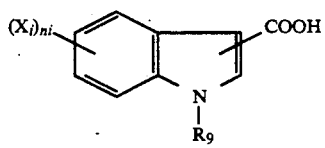

in which $R_9$ represents an alkoxycarbonylalkyl group may be prepared from indolecarboxylic acids which are available commercially or are obtained by conventional processes, in accordance with the reaction scheme (a)

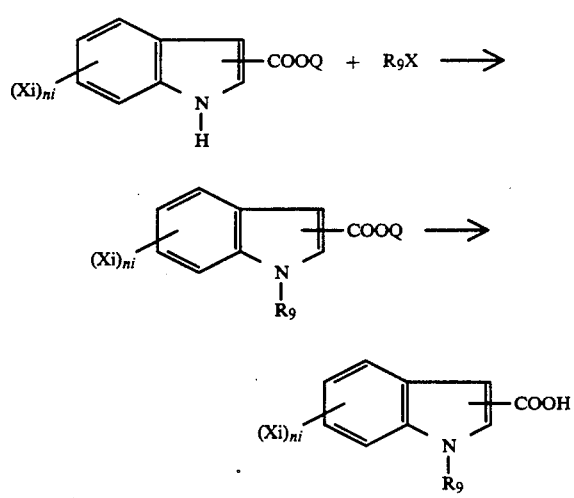

in which X represents a halogen atom and Q represents the benzyl group.

The benzyl esters in scheme (a) are prepared by reacting the corresponding acid on benzyl alcohol, in the presence of one of the agents for activating the acid functions which are commonly used in peptide synthesis, such as:

1,2′-carbonyldiimidazole, for which reference may be made to Synthesis p. 833 (1982), N,N′-dicyclohexylcarbodiimide in the presence of 4-(dimethylamino)pyridine, for which reference may be made to J. Org. Chem. 55 (4) p. 1390 (1990), N-ethyl-N′-[3-(dimethylamino)propyl]carbodiimide in the presence of 4-(dimethylamino)pyridine, for which reference may be made to J. Org. Chem. 47 1962 (1982), N,N-bis(2-oxo-3-oxazolidinyl)phosphorodiamide chloride, for which reference may be made to Synthesis p. 547 (1980), and benzotriazolyloxy-tris-(dimethylaminophosphonium) hexafluorophosphate, for which reference may be made to Synthesis p. 413 (1977).

The acid activated in this way may also be isolated before reacting it with benzyl alcohol.

The benzyl esters in scheme (a) may also be prepared by reaction of indolecarboxylic acid and alcohol, activated as phosphonium derivatives, as is described in Tetrahedron 36 p. 2409 (1980) or in Synthesis p. 1 (1981).

The base used in fixing $R_9$ on the nitrogen of the benzyl ester is preferably an anhydrous strong base, such as an alkali metal hydride; the reaction medium is then a polar aprotic solvent stable in the presence of a strong base, such as dimethylformamide or dimethoxyethane; the reaction is carried out at a temperature of between 15° C. and 80° C. approximately.

The removal of the benzyl group, after the N-alkylation, is carried out in a conventional manner by the action of at least one equivalent of hydrogen, in the presence of a catalyst, such as palladium-on-charcoal, on the ester in solution in an alcohol or dimethylformamide, if necessary under a slight pressure.

The indolecarboxylic acids of formula Z″COOH in which $R_9$ represents a hydroxyalkyl, alkoxyalkyl, aminoalkyl, cyanoalkyl or carbamoylalkyl group may be prepared in accordance with reaction scheme (a) in which Q represents a $C_1$ to $C_3$ alkyl group; the hydrolysis of the ester can then, in fact, be carried out in an acid or basic medium and, for example, by the action of an inorganic base in an aqueous/alcoholic medium at a temperature of between 40° C. and the reflux temperature of the solvent, without modification of $R_9$.

In addition, some of the acids ZCOOH are of low stability or carry a function which could react during the condensation reaction with the aminothiazole and it is preferable to use these in a protected form Z′COOH.

Thus, compounds (I) in which Z represents

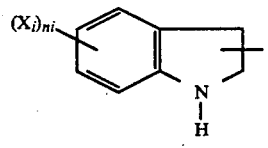

and in which $(X_i)_{ni}$ represents the optical substituents, may be prepared from compounds obtained by a coupling reaction of the aminothiazole with indolinylcarboxylic acid Z′COOH, of formula

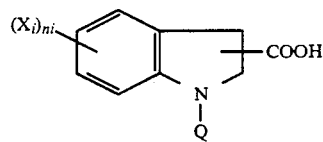

in which Q represents a group generally used for the protection of $NH_2$ groups in the condensation reactions of amino acids, such as $COO(t-C_4H_9)$; the protective group Q may be removed from the compound of formula V

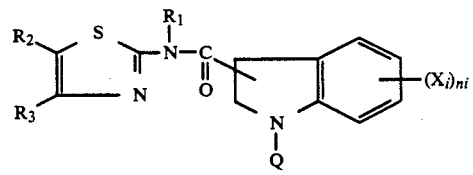

obtained after the coupling reaction with compound (II), by reaction of a strong acid in an anhydrous medium, such as $CF_3CO_2H$ in $CH_2Cl_2$ or HCl in $CH_3CO_2C_2H_5$.

It has been found that in the case where Z represents

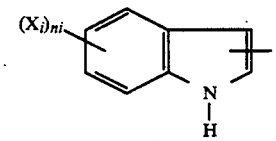

the nitrogen of the indolecarboxylic acid may be protected for the coupling reaction with the aminothiazole by a tetrahydropyranyl group, an acyl group, such as acetyl, or a carboxylic group, such as benzyloxycarbonyl or tert-butoxycarbonyl; these protective groups are fixed on the nitrogen and then removed, after the coupling reaction using methods known per se and, for example, by reaction of an aqueous dilute acid solution on the tetrahydropyranyl derivative, by reaction of an anhydrous acid on the t-butylcarbamate, by catalytic hydrogenation in the case of the benzylcarbamate or by hydrolysis of the acetyl derivative in a basic medium.

The acids Z″COOH in which $R_9$ is $COOC(CH_3)_3$ or $COOCH_2C_6H_5$ may be prepared by reaction of the corresponding chloroformate $ClCOOC(CH_3)_3$ or $ClCOOCH_2C_6H_5$ on Z″COOH in which $R_9$=H, in the presence of a base such as triethylamine and 4-(dimethylamino)pyridine, in a solvent such as acetonitrile or methylene chloride.

The acids Z″COOH in which $R_9$ is an acyl group may be prepared by reaction of the acid chloride or acid anhydride with Z″COOH in which $R_9$=H in the presence of one equivalent of triethylamine and 4-(dimethylamino)pyridine, for example in methylene chloride.

The acid chlorides of formula ZCOCl, Z′COCl or Z″COCl may be prepared, in particular, by reaction of $SOCl_2$ or of a mixture of $POCl_3$ and $P_2O_5$ with the corresponding acid, in general in the absence of solvent and at the reflux temperature of the mixture.

The mixed anhydrides of formula ZCOOCOY′, Z′COOCOY′ or Z″COOCOY′, in which Y′ represents a $C_1$ to $C_4$ alkyl group, may be prepared by reaction of an alkyl chloroformate with the acid, in the presence of a base, generally a tertiary amine such as triethylamine; this reaction is most often carried out in a solvent such as dichloromethane, dichloroethane or chloroform.

Amongst the activated esters of formula ZCOOY", Z'COOY" or Z"COOY", those in which Y" represents

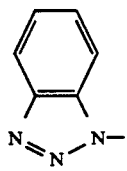

may be prepared by reaction of 1-hydroxybenzotriazole with the acid in the presence of dicycohexylcarbodiimide in accordance with the method described in J. Am. Chem. Soc. 93, 6318-6319 (1971), or by reaction of benzotriazolyl-1-oxytris(dimethylamino)phosphonium hexafluorophosphate in accordance with the method described in Synthesis 751-752 (1976); and those in which Y" represents

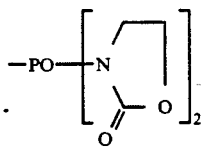

may be prepared by reaction of N,N-bis(2-oxo-3-oxazolidinyl)phosphorodiamide chloride in accordance with the method described in J. Am. Chem. Soc. 107, 4342-4343 (1985).

The coupling reaction of the aminothiazole (II) with the acid in the form of the activated ester may be carried out in a solvent, the nature of which is chosen depending on the solubility of the compounds and the type of activation of the acid group, preferably in the presence of a base, for example a tertiary amine such as triethylamine; the reaction is generally carried out at a temperature of between 0° C. and 30° C.

When the compounds of formula I comprise a carboxylic acid group in $R_1$ or Z, these compounds are prepared by hydrolysis of a corresponding ester of formula I, either in an acid medium or, preferably, in a basic medium, for example, by the action of an inorganic base, such as an alkali metal hydroxide, in an aqueous/alcoholic medium.

In the case where Z represents the indolyl group unsubstituted on the nitrogen, it is also advantageous to prepare the compound of formula (I) by dehydrogenation of the corresponding indolinyl compound of formula VI

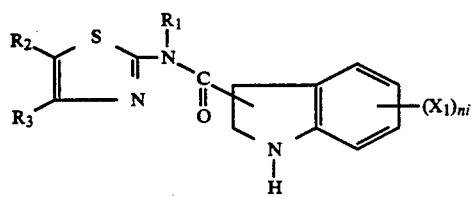

in which $R_1$, $R_2$, $R_3$ and $(X_i)_{ni}$ have the same meanings as above.

The reaction is carried out by means of a conventional dehydrogenating reagents, such as 2,3,5,6-tetrachloro-1,4-benzoquinone (p-chloranil), 2,3-dichloro-5,6-dicyano-1,4-benzoquinone (DDQ) or cyclohexene, in the presence of Pd in inert solvents having a high boiling point, such as diphenyl ether, xylene, 1,2-dimethoxyethane or 2-methoxyethyl ether at elevated temperature and preferably at the reflux temperature of the solvent.

The addition salts of compounds of formula I with acids or bases are prepared in the usual way by introduction of the acid, or of the base, into a solution of the compound of formula I. The salt is isolated, depending on its solubility characteristics, after evaporation of the solvent or addition of a non-solvent.

The compounds of formula I and their salts are cholecystokinin antagonists, which are to a greater or lesser extent selective for type A or type B receptors, and more or less powerful gastrin antagonists.

Their affinity for the CCK A receptor has been determined in vitro using the method described below, the principle of which is that indicated in Life Sciences 37 (26) 2483-2490 (1985); it consists in determining the removal of the iodated CCK 8S from its fixation receptors on a rat pancreas homogenate: aliquot amounts of pancreatic membrane suspension (100 μg of proteins per ml) in a TRIS.HCl (50 mM) buffer of pH 7.4 containing $MgCl_2$ (5 mM), bacitracin (0.1 mg/ml) and methylphenylmethanesulphonyl fluoride (0.1 mg/ml) are incubated for 40 minutes at 25° C. in the presence of iodated CCK 8S (2,000 Ci/mmole, or 50 pM final concentration) and increasing concentrations of the substance to be studied; the reaction is stopped at the end of 40 minutes by centrifuging. After removing the supernatant, the radioactivity of the deposit is measured. In addition, the non-specific binding is determined in the presence of CCK 8S in a concentration of 1 μM.

Under these conditions, the concentration inhibiting 50% of the binding ($CI_{50}$) is less than $10^{-7}$ M for the products of the invention, and of the order of $10^{-9}$ M for a large number of these, while under the same conditions the $CI_{50}$ of the carboxamic benzodiazepin mentioned in the beginning of the specification is about $10^{-8}$ M.

Their affinity for the CCK B receptors was determined by studying the removal of iodated CCK 8S from its specific receptors present on guinea-pig cortex homogenates using the same method as for the CCK A receptors, but for a membrane suspension containing 600 μg of proteins/ml and using a HEPES (10 mM) buffer of pH 6.5 containing NaCl (130 mM), $MgCl_2$ (5 mM), EDTA (1 mM) and bacitracin (250 mg/l) and the incubation being for 2 hours.

At a concentration of $10^{-5}$ M, all of the products remove more than 25% of the labelled CCK 8S from the B receptor; some have $CI_{50}$ of about $10^{-6}$ M, lower than those of the racemic benzodiazepin-urea mentioned above.

The affinity for the gastrin receptor of those compounds which were the most specific for CCK B was studies in accordance with the method described below, the principle of which is that indicated in J. Receptor. Res. 3 (5) 647-655 (1983); : guinea-pig gastric gland aliquots in a HEPES (24.5 mM) buffer of pH 7.4 comprising NaCl (98 mM), KCl (6 mM), $NaH_2PO_4$ (2.5 mM), pyruvate (5 mM), glutamate (5 mM), $CaCl_2$ (0.5 mM), $MgCl_2$ (1mM), glucose (11.5 mM), glutamine (1 mM) and bovine albumin (0.4 g/100 ml) were incubated for 90 minutes at 37° C. in a water-bath in the presence of iodated gastrin (2-17) (2,000 Ci/mmol; 70 pM) and increasing concentrations of the products to be studied. The reaction was stopped by centrifuging and the radioactivity of the deposit was measured; the non-specific binding was determined in the presence of 1 μM gastrin (2-17). The compounds of the invention have a $CI_{50}$ of between $10^{-5}$ M and $10^{-8}$ M.

It has also been shown that the compounds of the invention have an activity antagonistic to that of CCK. This has been demonstrated in vitro by measuring the inhibition, by the products to be tested, of the secretion of amylase by the pancreatic acinar cells of rats stimulated by CCK 8S, in accordance with a method similar to that described in J. Bio. Chem. 254 (12) 5321-5327 (1979) but using guinea-pig pancreatic tissues. The compounds have a $CI_{50}$ of $10^{-6}$ to $10^{-7}$ M, the order of magnitude of the $CI_{50}$ of the racemic benzodiazepincarboxamide mentioned above.

Finally, in vivo, in mice, the compounds having a good affinity for the gastric receptors triggered the gastric emptying activity inhibited by the subcutaneous administration of CCK 8S in the protocol described in Life Sciences, 39 1631-1638 (1986); the $ED_{50}$ (effective dose 50) thus determined is distinctly lower than that of proglumide, a known gastrin antagonist.

As these compounds are of low toxicity, they can be used as medicines, for the treatment of physiological disorders resulting from hypersecretion of these peptides or from dysregulation of the biological hormonal systems in which they are involved, in the intestinal sphere or in the central nervous system, depending on their specificity. Reference may be made to the review of therapeutic applications of CCK and gastrin antagonists published in "Proceedings of International Symposium on Gastrin and Cholecystokinin" —7-11 Sep. 1987—Ed. J. P. Bali, J. Martinez—Elsevier Science Pub. BV.

In particular, the CCK antagonists will be useful in the treatment of intestinal dyskineses, such as irritable bowel syndrome, in the treatment of acute or chronic pancreatitis or in the treatment of pancreatic carcinomas, but also to regulate the appetite or, in combination with opiate analgesics, in the treatment of pain.

The more selective gastrin antagonists will be useful in the treatment and the prevention of gastric ulcers, in the treatment of Zollinger-Ellison syndrome and in the treatment of hyperplasia of G cells of the antrium or for cancers of the oesophagus, the stomach or the intestine.

Amongst the cholecystokinin antagonists acting on the A receptors, the following compounds are preferred:

N-[4-(2,4,6-trimethylphenyl)-2-thiazolyl]indole-2-carboxamide and its derivatives substituted on the indole nitrogen, in particular by ($C_1$-$C_4$) alkyl, such as $CH_3$, $CH_2COOR$, with R being H or ($C_1$-$C_4$) alkyl, in particular $CH_3$, and $(CH_2)_2NR_{10}R_{11}$ with $R_{10}$ and $R_{11}$ being ($C_1$-$C_4$) alkyl, such as $CH_3$, N-[4-(2,4,6-trimethoxyphenyl)-2-thiazolyl]-indole-2-carboxamide and its derivatives substituted on the indole nitrogen, in particular by ($C_1$-$C_4$) alkyl, such as $CH_3$, $CH_2COOR$, where R is H or ($C_1$-$C_4$) alkyl, such as $CH_3$, N-[4-(2,6-dimethylphenyl)-2-thiazolyl]-indole-2-carboxamide and its derivatives substituted on the indole nitrogen, in particular by $CH_2COOR$, R being H or ($C_1$-$C_4$) alkyl, such as $CH_3$, N-[4-(2,6-dimethoxyphenyl)-2-thiazolyl]-indole-2-carboxamide and its derivatives substituted on the indole nitrogen, in particular by $CH_2COOR$, R being H or ($C_1$-$C_4$) alkyl, such as $CH_3$, N-[4-(2,6-dichlorophenyl)-2-thiazolyl]-indole-2-carboxamide and its derivatives substituted on the indole nitrogen, in particular by $CH_2COOH$ and $(CH_2)_2NR_{10}R_{11}$, with $R_{10}$ and $R_{11}$ being ($C_1$-$C_4$) alkyl, such as $CH_3$, N-[4-(2-methylphenyl)-2-thiazolyl]-indole-2-carboxamide and its derivatives substituted on the indole nitrogen, in particular by $CH_2COOH$, N-[4-(2-methoxyphenyl)-2-thiazolyl]-indole-2-carboxamide and its derivatives substituted on the indole nitrogen, in particular by $CH_2COOH$, N-[4-(2-chlorophenyl)-2-thiazolyl]-indole-2-carboxamide and its derivatives substituted on the indole nitrogen, in particular by $CH_2COOR$, with R being H or ($C_1$-$C_4$) alkyl, such as $CH_3$, N-[4-(4-methylphenyl)-2-thiazolyl]-indole-2-carboxamide, and N-[4-(4-methoxyphenyl)-2-thiazolyl]-indole-2-carboxamide.

Amongst the cholecystokinin antagonists acting on the B receptors and the gastrin antagonists, the following compounds are preferred:

N-[4-(2,4,6-trimethoxyphenyl)-2-thiazolyl]-indole-2-carboxamide and its derivatives substituted on the indole nitrogen by $CH_2COOH$, with R being H or ($C_1$-$C_4$) alkyl, such as $CH_3$, N-[4-(2,6-dimethoxyphenyl)-2-thiazolyl]-indole-2-carboxamide and its derivatives substituted on the indole nitrogen by $CH_2COOR$, with R being H or ($C_1$-$C_4$) alkyl, such as $CH_3$, and N-[4-(2,4,6-trimethoxyphenyl)-2-thiazolyl]benzofuran-2-carboxamide.

The medicines according to the invention comprise at least one of the compounds of formula I or one of its salts with a pharmaceutically acceptable acid or base, optionally in combination with the usual excipients to give a pharmaceutical composition which can be administered in the usual way orally, transmucously, parenterally or rectally. The doses administered depend on the nature and the severity of the disease, on the compound and on the administration route. They will generally be between 20 and 100 mg per day for the adult human when administered orally and 3 to 10 mg when administered by injection.

For oral administration, the pharmaceutical compositions according to the invention can be in the form of tablets, pills, capsules or granules or of solution, suspension or gel. For parenteral administration, the compositions of the invention will be in the form of solution, suspension or emulsion in an oil or any injectable solvent, optionally water-based, containing the conventional adjuvants in this type of formulation.

For local application, on the skin or on the mucous membranes, the compositions according to the invention will be in the form of a cream or ointment or in the form of a transdermal device, while for rectal administration they will be in the form of a suppository or rectal capsule.

In the text which follows, examples of the invention are described, as well as the processes for the preparation of some synthetic intermediates of formula II and IV. The melting points indicated were determined in a capillary. The nuclear magnetic resonance (NMR) spectra were recorded relative to tetramethylsilane.

PREPARATION OF ALPHA-BROMOKETONES OF FORMULA IV

A) 2,4,6-Trimethylphenyl bromomethyl ketone (IV: $R_2$=H; $R_3$=2,4,6—$(CH_3)_3C_6H_2$—)

50 g of 2,4,6-trimethylphenyl methyl ketone are dissolved in 200 ml of glacial acetic acid and 31.8 g of bromine were added dropwise, keeping the reaction mixture at a temperature below 10° C. At the end of the addition, the temperature is allowed to return to ambient temperature and the mixture is left at this temperature for 2 hours. The reaction mixture is poured into 500 ml of ice-water and the aqueous phase is extracted with diethyl ether. The organic extracts are washed with a saturated aqueous sodium bicarbonate solution and then with salted water and dried over anhydrous magnesium sulphate. The evaporation of the solvent leaves an oil which is used without further purification in the subsequent step.

B) 2,4,6-Trimethoxyphenyl bromomethyl ketone (IV: $R_2$=H; $R_3$=2,4,6—$(OCH_3)_3C_6H_2$—)

A suspension of 45.3 g of cupric bromide $CuBr_2$ in 150 ml of ethyl acetate is brought to reflux and 25.1 g of 2,4,6-trimethoxyphenyl methyl ketone in solution in 150 ml of chloroform are added rapidly at this temperature. The appearance of an abundant greenish yellow precipitate is noted. The reaction mixture is left under reflux for 2 h 30. The temperature is then allowed to return to ambient temperature and the insoluble salts are filtered off and washed with ethyl acetate. The organic phases are treated with animal charcoal: after removal of the solid by filtration, the filtrate is concentrated under reduced pressure to obtain an oil, which is purified by chromatography on a silica column (eluant: cyclohexane/ethyl acetate, 6/4, V/V). Yield: 60%. Oil

C) Cyclohexyl brmomethyl ketone

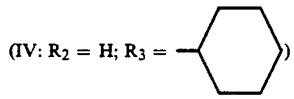

7.2 g of cyclohexanecarboxylic acid chloride are dissolved in 50 ml of diethyl ether. After cooling to 0° C., a solution of 0.1 mol of diazomethane in 100 ml of diethyl ether, prepared for immediate use from 21.5 g of p-tolylsulphonylmethylnitrosamide (Diazald ®) by the method described in Organic Synthesis Coll. Vo. IV p. 250, is added. The mixture is left at ambient temperature for 24 h.

9.1 ml of a 48% (m/V) aqueous hydrobromic acid solution are added to the diazoketone solution thus obtained, keeping the temperature of the reaction mixture at 0° C. Stirring is continued for about 12 hours at ambient temperature and the reaction mixture is poured into water. The organic phase is decanted and dried over anhydrous sodium sulphate. The evaporation of the solvent leaves an oil which is used without purification in the subsequent step.

D) 2,6-Dimethoxy-4-ethylphenyl chloromethyl ketone (IV $R_2$=H; $R_3$=2,6-$(OCH_3)_2$-4-$C_2H_5C_6H_2$ and Cl in place of Br)

83 g of 3,5-dimethoxyethylbenzene and 6.1 g of tetramethylenediamine are dissolved in 100 ml of hexane and 32.8 ml of butyl-lithium are added at 0° C. After 1 hour at 10° C., the cream suspension obtained is introduced into a solution of 6.1 g of N-methyl-N-methoxychloroacetamide in 50 ml of tetrahydrofuran, which is at −10° C. After 1 hour at a temperature below 0° C., the temperature is allowed to return to ambient temperature before adding 100 ml of water. The desired product is extracted with ethyl ether and purified by chromatography on silica gel. m.p.=72° C.

E) N-Methylpyrrolyl chloromethyl ketone 6

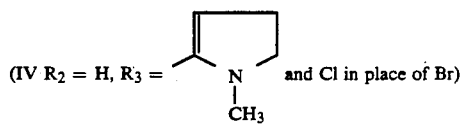

prepared in accordance with the method described in Synthesis p. 212-213 (1990). F) 2,5-Dimethoxy-4-hydroxyphenyl chloromethyl ketone and 2,4-dimethoxy-6-hydroxyphenyl chloromethyl ketone prepared in accordance with the method described in J. Chem. Soc. p. 3112 (1957).

The bromo-ketones in Table I were prepared using one of the processes used according to A or B.

TABLE I

| $R_2$ | $R_3$ | (compounds IV) Process | m.p. °C. | Yield |
|---|---|---|---|---|
| | —$H_2C$—$H_2C$—$H_2C$— (o-methylphenyl) | B | oil | 88% |
| | —$H_2C$—$H_2C$—$H_2C$— (3,4-dimethylphenyl) | B | oil | 92% |
| H | —C_6H_4—Cl | A | 57 | 100% |

TABLE I-continued (compounds IV)

| R₂ | R₃ | Process | m.p. °C. | Yield |
|---|---|---|---|---|
| H | 3,4-dichlorophenyl | A | 54 | 90% |
| H | 4-methylphenyl | A | 45 | 90% |
| H | 3,5-dimethylpyridyl | B | 252 (HCl) | 87% |
| H | 2,6-dichlorophenyl | A | oil | 96% |
| H | 4-methoxyphenyl | B | 70 | 85% |
| | —H₂C—H₂C—(2-methylphenyl) | B | oil | 90% |
| H | 2-methoxyphenyl | B | 45 | 95% |
| H | 2,4-dimethoxyphenyl | B | 102 | 92% |
| H | 3,5-dimethyl-4-methoxyphenyl (H₃C, CH₃, H₃CO) | B | 50 | 68% |
| H | 2,5-dimethoxyphenyl (H₃CO, H₃CO) | C | oil | 63% |

TABLE I-continued (compounds IV)

| $R_2$ | $R_3$ | Process | m.p. °C. | Yield |
|---|---|---|---|---|
| H | (H₃C)₂CH— aryl with CH(CH₃)₂ and (H₃C)₂CH substituents | A | oil | 90% |
| CH₃ | phenyl | A | oil | 90% |
| H | 2-methylthiophen-3-yl (H₃C, S) | B | oil | 87% |
| CH₃ | 2,4-dimethylphenyl (H₃C, CH₃) | B | b.p. = 74/35 Pa | 90% |
| H | 2-methylphenyl (H₃C) | A | oil | 80% |
| H | 2,6-dimethylphenyl (H₃C, H₃C) | A | oil | 97% |
| H | 3-methylphenyl (H₃C) | A | oil | 80% |
| H | 2-chlorophenyl (Cl) | B | oil | 70% |
| H | 3,5-dimethyl-4-(NHCOCH₃)phenyl (H₃C, H₃C, NHCOCH₃) | B | 146 | 80% |
|  | —H₂C—CH₂— aryl with OCH₃, CH₃, CH₃O substituents | A |  |  |

TABLE I-continued

| R$_2$ | R$_3$ | (compounds IV) Process | m.p. °C. | Yield |
|---|---|---|---|---|
| H | 3,4,5-trimethoxyphenyl (OCH$_3$, OCH$_3$, OCH$_3$) | A | | |
| H | 2-(trifluoromethyl)phenyl (F$_3$C) | A | b.p. = 80/350 Pa | 76% |

PREPARATION OF AMINOTHIAZOLES OF FORMULA II a) 2-Amino-4-(2,4,6-trimethylphenyl)thiazole

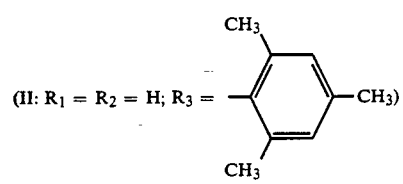

(II: R$_1$ = R$_2$ = H; R$_3$ = 2,4,6-trimethylphenyl)

A solution of 80 g of 2,4,6-trimethylphenyl bromoethyl ketone and 35 g of thiourea in 250 ml of methanol is refluxed for 3 hours. After cooling the reaction mixture, the precipitate is filtered off and washed abundantly with diethyl ether. After concentration of the filtrate to a third of the initial volume, a second bath of crystals is recovered. Yield: 70%. m.p.=138° C. The hydrobromide prepared by the action of HBr in ethanol melts at 295° C.

b) 4-(2,4,6-Trimethoxyphenyl)-2-methylaminothiazole

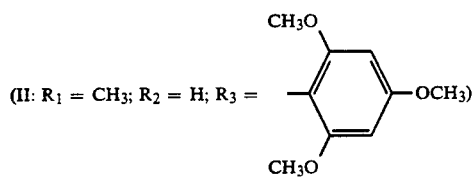

(II: R$_1$ = CH$_3$; R$_2$ = H; R$_3$ = 2,4,6-trimethoxyphenyl)

A mixture of 5 g of 2,4,6-trimethoxyphenyl bromomethyl ketone and 1.72 g of N-methylthiourea in 40 ml of methanol is refluxed for 8 hours. The reaction mixture is evaporated to dryness and the crystals obtained are recrystallised from ethanol. Yield: 83%.

Melting point of the hydrobromide 246° C.

The aminothiazoles of formula II in which R$_1$=H, which are shown in Table II, were prepared by applying the above processes.

TABLE II

| R$_2$ | R$_3$ | (compounds II; R$_1$ = H) m.p. °C. (salt) | Yield |
|---|---|---|---|
| H | —CH$_2$—CH$_2$—CH$_2$—phenyl | 206 (HBr) | 50% |
| H | —CH$_2$—CH$_2$—CH$_2$-(2,5-dimethylphenyl) | 230 (HBr) | 80% |
| H | 3,4,5-trimethoxyphenyl | 225 (HBr) | 87% |
| H | cyclohexyl | 146 | 70% |
| H | 4-chlorophenyl | 166 (HBr) | 53% |
| H | 2,3-dichlorophenyl | 180 (HBr) | 55% |
| H | 2,6-dimethylpyridin-4-yl | 240 (HBr) | 86% |
| H | 2,4-dichlorophenyl | 210 (HBr) | 60% |

TABLE II-continued
(compounds II; R₁ = H)
| R₂ | R₃ | | m.p. °C. (salt) | Yield |
|---|---|---|---|---|
| H | 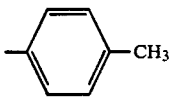 | | 134 (HBr) | 62% |
| H | 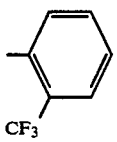 | | 167 (HBr) | 86% |
| H | 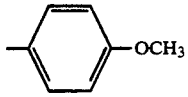 | | 240 (HBr) | 88% |
| | 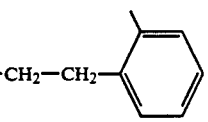 | | 250 (HBr) | 67% |
| H | 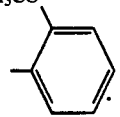 | | 240 (HBr) | 72% |
| H | 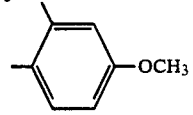 | | 265 (HBr) | 82% |
| H | 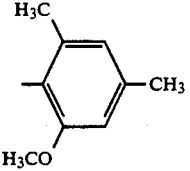 | | 238 (HBr) | 65% |
| H | 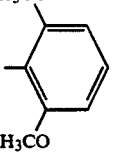 | | 270 (HBr) | 84% |
| CH₃ | 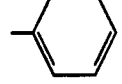 | | 117 | 50% |
| H | 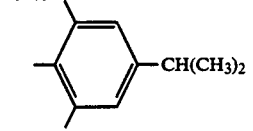 | | 200 (HBr) | 33% |
| H | 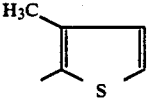 | | 128 | 77% |
| CH₃ | 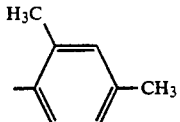 | | 172 (HBr) | 93% |
| H | 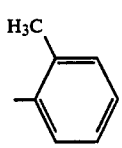 | | 188 (HBr) | 80% |
| H | 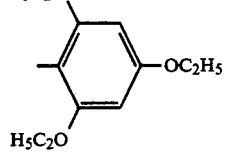 | | 210 | 70% |
| H | 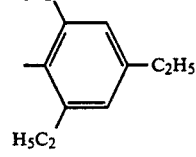 | | 134 | 28% |
| H | 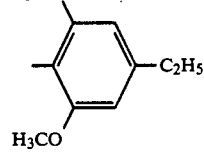 | | 163 | 65% |
| | 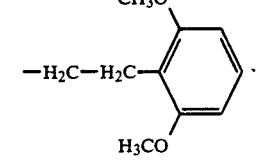 | | >260 (HBr) | 78% |
| H | 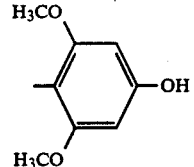 | | >250 (HCl) | 76% |
| H | 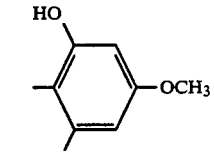 | | 236 (HCl) | 95% |
| H | 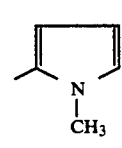 | | 199 (HCl) | 70% |

TABLE II-continued (compounds II; $R_1 = H$)

| $R_2$ | $R_3$ | m.p. °C. (salt) | Yield |
|---|---|---|---|
| H | (2-chlorophenyl)methyl | 140 | 88% |
| H | (4-acetamido-3,5-dimethylphenyl)methyl | 208 (HCl) | 70% |
| H | (3,5-dimethylphenyl)methyl | 196 (HBr) | 70% |

PREPARATION OF INDOLECARBOXYLIC ACIDS

A') Benzyl indole-2-carboxylate 5 g of N,N'-carbonyldiimidazole are introduced into a solution of 5 g of indole-2-carboxylic acid in 50 ml of dry tetrahydrofuran; after stirring for 12 hours at ambient temperature, 3.7 g of benzyl alcohol are added and the reaction mixture is brought to its reflux temperature; this is maintained for 8 hours, before removing the solvent by distillation under reduced pressure. The residue is dissolved in ethyl acetate and the organic phase is washed with a N aqueous NaOH solution and then dried before evaporation of the solvent.

The yellow residue is recrystallised from isopropanol. m.p.=136° C.; yield 85%.

B') Benzyl (1-methoxycarbonylmethyl)indole-2-carboxylate

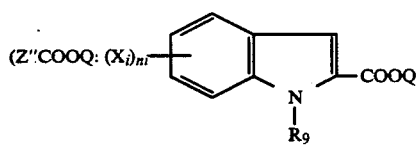

$R_9 = CH_2COOCH_3; X_i = H; Q = C_6H_5$.

5 g of benzyl indole-2-carboxlate in solution in 20 ml of dimethylformamide are introduced slowly into 30 ml of a suspension of 1 g of NaOH in 30 ml of dimethylformamide and 3.1 g of methyl bromoacetate are then introduced. After 12 hours at ambient temperature, with stirring, the mixture is poured into a volume of ice-water and then extracted with ethyl acetate. The dried organic phase is concentrated and the residue is recrystallised from aqueous ethanol (95%, V/V). m.p.=94° C.; yield 87%.

C') 1-(Methoxycarbonylmethyl)indole-2-carboxylic acid (Z"COOH:R$_9$=CH$_2$COOOCH$_3$).

3g of the ester obtained according to B') are dissolved in a mixture of 50 ml of ethanol and 10 ml of dimethylformamide, and 300 mg of palladium-on-charcoal (5%) are added. The mixture is hydrogenated at ambient temperature under a pressure of 0.1 MPa. When the absorption of hydrogen has ceased, the mixture is degassed and filtered on a bed of talc. The residue obtained after evaporation of the solvents is washed with diisopropyl ether. m.p.=194° C.; yield 90%.

D') 1-(2-N,N-Dimethylamino)ethyl)indole-2-carboxylic acid (Z"COOH:R$_9$=(CH$_2$)$_2$N(CH$_3$)$_2$)

a) ethyl ester 2.8 g of NaH are introduced, in portions, in an inert atmosphere into a solution of 5 g of ethyl indole-2-carboxylate in 40 ml of dimethylformamide; at the end of the evolution of H$_2$, 4.2 g of N-(2-chloroethyl)-N,N-dimethylamine hydrochloride are added in portions. After stirring for 12 hours at ambient temperature, the reaction mixture is poured into a volume of ice-water and then extracted with ethyl acetate. The dried organic phase is evaporated to dryness. Oil—yield 90%.

b) acid 6 g of the oil obtained in a) are dissolved in 50 ml of aqueous ethanol (95%, V/V) with 2 g of KOH in pellets. The reaction mixture is kept at its reflux temperature for 1 hour and the solvent is then removed under reduced pressure. The residue is dissolved in 150 ml of water and carbon dioxide gas is bubbled through the mixture for 1 hour. The precipitate formed is isolated. m.p.=228° C.; yield 83%.

E')

1-(3-(N,N-Dimethylamino)propyl)indole-2-carboxylic acid (R$_9$=(CH$_{2ll}$)$_3$N(CH$_3$)$_2$) prepared in accordance with the process described in D')

m.p. =160° C; yield 70%.

F') 1(2-Methoxyethyl)indole-2-carboxylic acid (Z"COOH:R$_9$=CH$_2$CH$_2$OCH$_3$)

1.4 g of sodium hydride are suspended in 10 ml of dimethylformamide and a solution of 5 g of ethyl indole-2-carboxylate dissolved in 25 ml of dimethylformamide is added dropwise. After one hour at ambient temperature, the mixture is cooled to 5° C. and 4.04 g of 1-methoxy-2-bromoethane are added; after 12 hours at ambient temperature, the mixture is brought to 60° C. for 1 hour and then, after cooling, is poured into a volume of ice-water; the mixture is extracted with ethyl acetate and, after drying, the organic phase is concentrated.

The residue obtained is taken up in 50 ml of ethanol containing 1.7 g of sodium hydroxide and the mixture is brought to the reflux temperature of the solvent for 2 hours.

The solution is then poured into a volume of water and acidified to pH=2 by addition of a N aqueous HCl solution. The desired acid precipitates. m.p. =150° C.; yield 82%.

G') 1-(2-Tetrahydropyranyl)indole-2-carboxylic acid (Z"COOH:R9=2-tetrahydropyranyl).

1.5 g of sodium hydride are added, in portions, to a solution of 5 g of ethyl indole-2-carboxylate in 40 ml of dimethylformamide; when the emission of gas has ceased, the mixture is cooled to 0° C. and 4.5 g of 2-chlorotetrahydropyran dissolved in 10 ml of dimethylformamide are introduced slowly. After stirring for 12 hours at ambient temperature, the mixture is poured into a volume of ice-water and then extracted with ethyl acetate. The organic phase is dried and concentrated to given an oil, consisting of ethyl 1-(2-tetrahydropyuranyl)-indole-2-carboxylate, in 95% yield.

2-Chlorotetrahydropyran was prepared by saturation of dihydropyran with HCl at 0° C.; boiling point 40° C. under 2,000 Pa.

The oily ester is introduced into 80 ml of ethanol containing 1.6 g of NaOH in pellets; the mixture is brought to its reflux temperature for 1 hour and the solvent is then distilled under reduced pressure. The residue is dissolved in 50 ml of water and the solution is then treated with 10 g of a cation exchange resin in H+ form (Amberlite® IRN77), before extraction with ethyl acetate.

The dried organic phase is brought to dryness and the residue is recrystallised from ethyl acetate. m.p.=216° C.; yield 86%.

H') 1-(t-Butoxycarbonyl)indole-2-carboxylic acid 30 ml of a solution in acetonitrile of 6 g of ditert-butyl dicarbonate are introduced dropwise into 30 ml of a solution of 4 g of indole-2-carboxylic acid, 4 ml of triethylamine and 0.4 g of 4-(dimethylamino)pryidine. After stirring for 2 hours at ambient temperature and removing the precipitate formed, the acetonitrile is removed by distillation and the residue is dissolved in methylene chloride. The organic phase is washed with water, dried and concentrated to dryness. m.p.=117° C.; yield: 66%.

I') 1-Benzyloxycarbonylindole-2-carboxylic acid

This compound, which melts below 40° C., is obtained by applying the above method.

EXAMPLE 1

N-[4-(4-Methoxyphenyl)-2-thiazolyl]-1-methyl-indole-2-carboxamide (I: $R_1 = R_2 = H$; $R_3 =$ 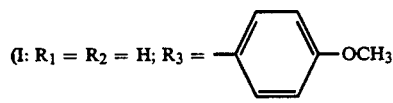

Z = 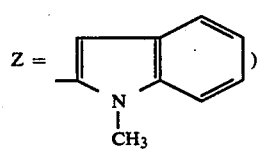)

1 g of 2-amino-4-(4-methoxyphenyl)thiazole is dissolved in 20 ml of dimethylformamide and, successively, 0.6 g of 1-methylindole-2-carboxylic acid, then 1.6 g of 1-benzotriazolyl-oxytris(dimethylamino)phosphonium hexafluorophosphate (BOP) and then 0.7 g of triethylamine are added to the reaction mixture at ambient temperature. The reaction mixture is left at ambient temperature for about 12 hours, while stirring well, before pouring into 100 ml of ice-water; the aqueous phase obtained is then extracted with twice 50 ml of ethyl acetate. The organic extracts are dried over anhydrous magnesium sulphate and evaporated to dryness. The residual solid is purified by chromatography on a silica column (eluant: $CH_2Cl_2$). Yield 25%. m.p.: 100° C.

$^1$H NMR: (250 MHz, DMSOd6): δ(ppm): 3.8(s,3H); 4.1(s,3H); 6.9–8.0 (m,10H); 12.7(s,1H).

EXAMPLE 2

N-Methyl-N-[4-(2,4,6-trimethylphenyl)-2-thiazolyl]-quinoline-3-carboxamide (I: $R_1 = CH_3$; $R_2 = H$; $R_3 =$ 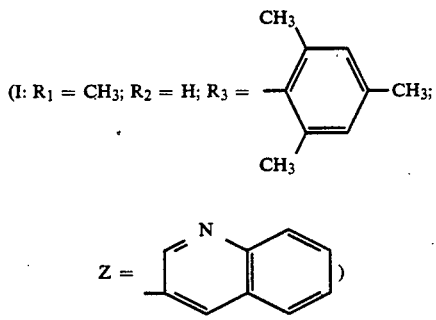

1 g of 2-[N-methyl-[4-(2,4,6-trimethylphenyl)]-amino]thiazole is dissolved in 20 ml of dimethylformamide and 1.6 g of triethylamine are added and a solution of 0.73 g of quinolyl-3-carboxylic acid chloride hydrochloride dissolved in 10 ml of dimethylformamide is then introduced dropwise, with stirring. The reaction mixture is then brought to 50° C. for 2 hours before evaporating to dryness and taking up the residue in 100 ml of dichloromethane. The organic solution is washed with water and dried over anhydrous magnesium sulphate before evaporating the solvent; the oily residue is purified by flash chromatography (silica, eluant: ethyl acetate/dichloromethane, 1/9). Yield: 45%.

The trifluoroacetate prepared by reaction of one equivalent of $CF_3COOH$ with the amine in solution in dichloromethane melts at 160° C.

$^1$H NMR: 80 MHz(DMSOd6)E(ppm): 2.2(s,6H; 2.4(s,3H); 3.8(s,3H); 7.0(s,2H); 7.3(s,1H); 7.7–8.3(m,4H); 8.9(s,1H); 9.3(s,1H).

The following examples described in Table III were prepared by applying the process of Example 1.

TABLE III

Compounds of formula I

| Ex. | R₁ | R₂ | R₃ | Z | m.p. °C. | Yield |
|---|---|---|---|---|---|---|
| 3 | H | H | 2,4,6-trimethylphenyl | quinolin-3-yl | 220 | 59% |
| 4 | H | H | 2,4,6-trimethylphenyl | 1-methylindol-2-yl | 278 | 27% |
| 5 | H | H | 2,4,6-trimethylphenyl | 1H-indol-2-yl | 328 | 44% |
| 6 | H | H | 2,4,6-trimethylphenyl | quinolin-2-yl | 196 | 50% |
| 7 | H | H | 2,4,6-trimethylphenyl | isoquinolin-1-yl | 252 | 45% |
| 8 | H | H | 4-methylphenyl | quinolin-3-yl | 210 | 35% |
| 9 | H | | —CH₂—CH₂—(2-methylphenyl) | quinolin-3-yl | 270 | 60% |
| 10 | H | | —CH₂—CH₂—(2-methylphenyl) | 1-methylindol-2-yl | 242 | 26% |
| 11 | H | | —CH₂—CH₂—CH₂—(2-methylphenyl) | quinolin-3-yl | 265 | 56% |

TABLE III-continued

Compounds of formula I

| Ex. | R₁ | R₂ | R₃ | Z | m.p. °C. | Yield |
|---|---|---|---|---|---|---|
| 12 | H | | −CH₂−CH₂−CH₂−(o-tolyl) | indole (NH) | 276 | 12% |
| 13 | H | | −CH₂−CH₂−CH₂−(o-tolyl) | N-methyl indole | 202 | 40% |
| 14 | H | H | 2,4,6-trimethoxyphenyl (H₃CO, OCH₃, H₃CO) | quinoline | 250 | 75% |
| 15 | H | H | 2,4,6-trimethoxyphenyl | N-methyl indole | 230 | 45% |
| 16 | H | H | 4-methoxyphenyl (−OCH₃) | quinoline | 310 | 72% |
| 17 | H | H | 4-chlorophenyl (−Cl) | quinoline | 346 | 44% |
| 18 | H | H | 2,6-diisopropyl-4-isopropylphenyl | N-methyl indole | 256 | 44% |
| 19 | H | H | 2,5-dimethylpyrrol-1-yl | quinoline | 150 | 12% |
| 20 | H | H | 2,4,6-trimethoxyphenyl (CH₃O, OCH₃, CH₃O) | N-COOC(CH₃)₃ indole | 140 | 10% |

TABLE III-continued

Compounds of formula I

| Ex. | R₁ | R₂ | R₃ | Z | m.p. °C. | Yield |
|---|---|---|---|---|---|---|
| 21 | H | H | 3,4,5-triethoxyphenyl (H₅C₂O, OC₂H₅, H₅C₂O) | indole-N-COOCH₂C₆H₅ | 250 | 30% |
| 22 | H | | -CH₂-CH₂-(2,5-dimethoxyphenyl with OCH₃, H₃CO) | indole-N-COCH₃ | 218 | 70% |
| 23 | H | H | 3,5-dimethoxy-4-ethylphenyl (H₃CO, C₂H₅, H₃CO) | indole-N-COCH₃ | 216 | 85% |
| 24 | H | H | 3,4,5-trimethoxyphenyl (H₃CO, OCH₃, H₃CO) | 3-substituted indole-N-COCH₃ | >250 | 14% |
| 25 | H | H | 3,4,5-trimethoxyphenyl (H₃CO, OCH₃, H₃CO) | indole-N-COCH₃ | 170 | 63% |
| 26 | H | H | 3,4,5-trimethoxyphenyl (H₃CO, OCH₃, H₃CO) | benzofuran-O | 170 | 80% |
| 27 | H | H | 3,4,5-trimethoxyphenyl (H₃CO, OCH₃, H₃CO) | 3-methylbenzofuran-O (H₃C) | 100 | 76% |
| 28 | H | H | 3,4,5-trimethoxyphenyl (H₃CO, OCH₃, H₃CO) | thieno[2,3-b]pyridine (N, S) | 220 | 20% |

TABLE III-continued

Compounds of formula I

| Ex. | R₁ | R₂ | R₃ | Z | m.p. °C. | Yield |
|---|---|---|---|---|---|---|
| 29 | H | H | 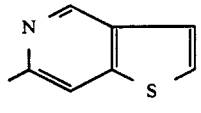 | 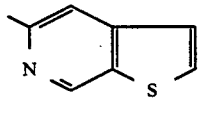 | 242 | 14% |
| 30 | H | H | 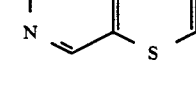 | 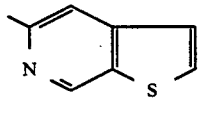 | >250 | 11% |
| 31 | H | H | 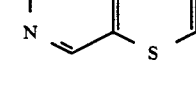 | 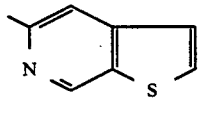 | >250 | 37% |

EXAMPLE 32

N-[4-(2,6-Dimethoxy-4-ethylphenyl)-2-thiazolyl]indole-2-carboxamide

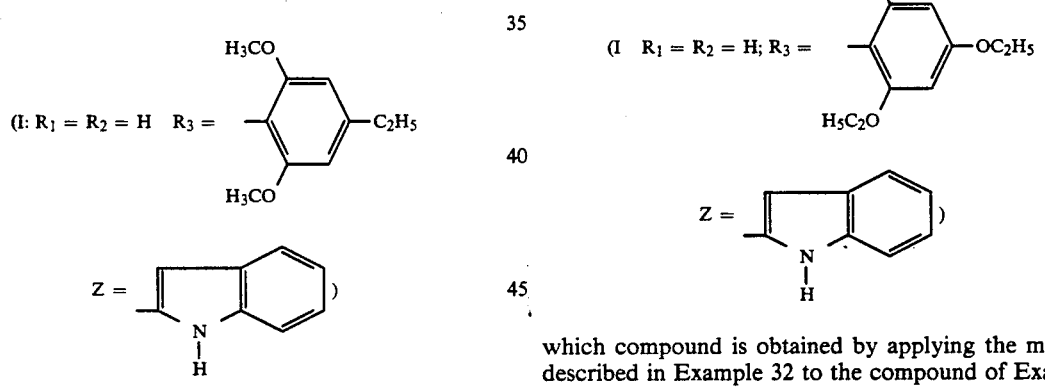

10 ml of 2N aqueous NaOH solution are introduced into a suspension of 1.4 g of the compound of Example 23

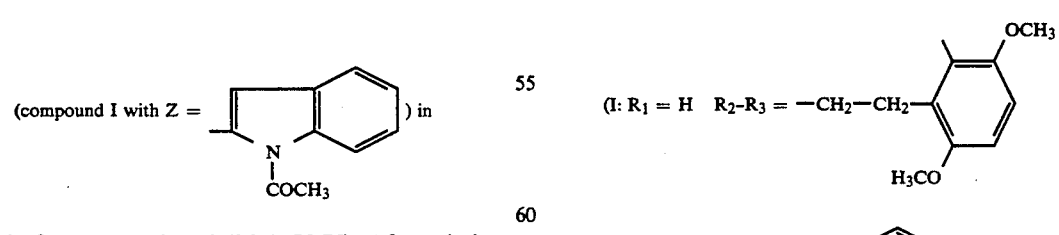

150 ml of aqueous ethanol (96%, V/V). After stirring for 2 hours at ambient temperature, 1.9 ml of a concentrated aqueous solution of hydrochloric acid are added. The precipitate formed is isolated and washed with ethanol and then with isopropyl ether. m.p.>260° C. yield: 85%.

EXAMPLE 33

N-[4-(2,4,6-triethoxyphenyl)-2-thiazolyl]indole-2-carboxamide

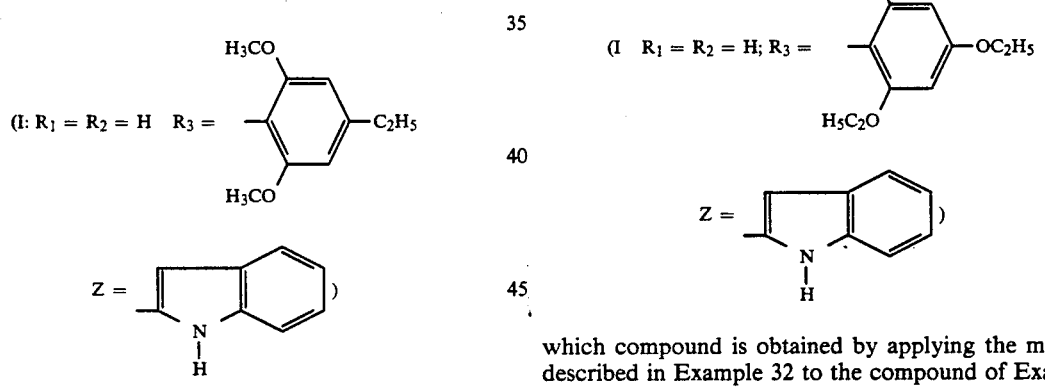

which compound is obtained by applying the method described in Example 32 to the compound of Example 21. m.p.=270° C. yield: 90%.

EXAMPLE 34

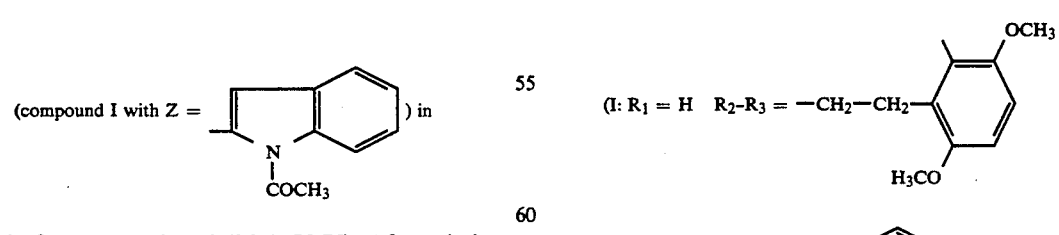

which compound is obtained from the compound of Example 22 by applying the process of Example 32. m.p.>260° C. Yield: 80%.

EXAMPLE 35

N-[4-(2,4,6-Trimethylphenyl)-2-thiazolyl]-1-tert-butoxycarbonyl-indoline-2-carboxamide.

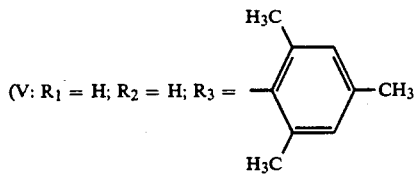

(V: $R_1$ = H; $R_2$ = H; $R_3$ =

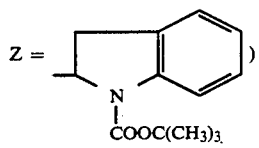

Z = )

21 g of 1-tert-butoxycarbonyl-indoline-2-carboxylic acid, then 35.2 g of 1-benzotriazolyl-oxytris (dimethylamino)phosphonium hexafluorophosphate (BOP) and the 24.2 g of triethylamine are added successively to a solution of 23.5 g of 2-amino-4-(2,4,6-trimethylphenyl)thiazole hydrobromide in 250 ml of dimethylformamide. The reaction mixture is stirred at ambient temperature for 12 h. The solvent is then evaporated under reduced pressure and 150 ml of ethyl acetate are poured onto the residue. The organic solution is washed with a saturated aqueous NaCl solution and dried over anhydrous magnesium sulphate. The solid obtained after evaporation of the solvent is washed with diisopropyl ether. Yield: 95%.

m.p.=206° C.

The compounds of formula V in Table IV, for which

Z represents 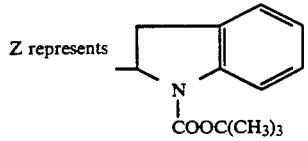

are prepared in accordance with this process.

TABLE IV

| Ex. | $R_1$ | $R_2$ | $R_3$ | m.p. °C. | Yield |
|---|---|---|---|---|---|
| 36 | H | H | —⟨⟩—CH₃ | 200 | 74% |
| 37 | H | H | H₃C-pyridyl-CH₃ | 206 | 75% |
| 38 | H | H | —⟨⟩—Cl | 230 | 32% |
| 39 | H | H | 2,3-diCl-phenyl | 206 | 89% |
| 40 | H | H | 3,4-diCl-phenyl | 203 | 71% |
| 41 | H | CH₃ | —⟨⟩ | 208 | 42% |
| 42 | H | | —CH₂—CH₂—⟨⟩ | 250 | 67% |

TABLE IV-continued

| Ex. | R₁ | R₂ | R₃ | m.p. °C. | Yield |
|---|---|---|---|---|---|
| 43 | H | | —CH₂—CH₂—CH₂—(2-methylphenyl) | 270 | 70% |
| 44 | H | | —CH₂—CH₂—CH₂—(2,4-dimethylphenyl with additional CH₃) | 200 | 95% |
| 45 | H | H | cyclohexyl | 174 | 74% |
| 46 | H | H | 2,4,6-trimethoxyphenyl (H₃CO, OCH₃, H₃CO) | 205 | 95% |
| 47 | H | H | 4-methoxyphenyl | 216 | 73% |
| 48 | H | H | 2-methoxyphenyl | 195 | 95% |
| 49 | H | H | 2,4-dimethoxyphenyl | 198 | 90% |
| 50 | H | H | 2,6-dimethoxyphenyl | 189 | 95% |
| 51 | H | H | 2,5-dimethyl-4-methoxyphenyl (H₃C, CH₃, H₃CO) | 190 | 73% |
| 52 | H | H | 2,4,6-triisopropylphenyl ((H₃C)₂HC, CH(CH₃)₂, (H₃C)₂CH) | 230 | 80% |

TABLE IV-continued

| Ex. | R₁ | R₂ | R₃ | m.p. °C. | Yield |
|-----|----|----|----|----------|-------|
| 53 | H | H | 3,4,5-tri(OCH₃)phenyl | 136 | 70% |
| 54 | H | CH₃ | 2,6-di(CH₃)phenyl | 125 | 60@ |
| 55 | H | CH₃ | 4-OCH₃-phenyl | 174 | 95% |
| 56 | CH₃ | H | 2,4,6-tri(OCH₃)phenyl | 91 | 80% |
| 57 | H | CH₃ | 4-Cl-phenyl | 206 | 92% |
| 58 | H | H | 2,4-di(CH₃)phenyl | 150 | 70% |
| 59 | H | H | 2,4,6-tri(CH(CH₃)₂)phenyl | 230 | 90% |

EXAMPLE 60

N-[4-(2,4,6-Trimethylphenyl)-2-thiazolyl]indoline-2-carboxamide

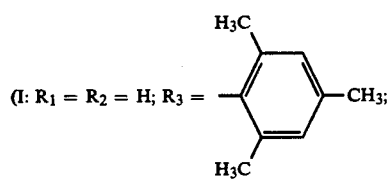

(I: R₁ = R₂ = H; R₃ =

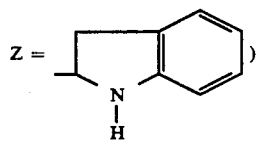

Z =  )

35 g of N-[4-(2,4,6-trimethylphenyl)-2-thiazolyl]-1-tert-butoxycarbonyl-indoline-2-carboxamide are dissolved in 200 ml of dry dichloromethane and 40 ml of trifluoroacetic acid are added dropwise. The reaction mixture is kept at ambient temperature for 2 hours and then evaporated to dryness. The residue obtained is taken up in 150 ml of ethyl acetate. The organic solution is washed with 1N aqueous sodium hydroxide solution and then with water saturated with NaCl and dried over anhydrous magnesium sulphate. After removal of the ethyl acetate, the final product is obtained, from which the salt is prepared by the action of gaseous HCl in isopropanol. The hydrochloride melts at 212° C. Yield 88%. Salt: ¹H NMR: 80 MHz(DMSOd6) δ(ppm): 2.1(s,6H); 2.4(s,3H); 3.2–3.8(m,2H); 5.0(m,1H); 6.0(s,1H; 6.9–7.6(m,7H); 12.1(s,1H).

EXAMPLE 61

N-[4-(4-Methoxyphenyl)-2-thiazolyl]indoline-2-carboxamide

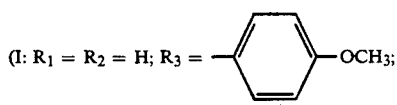

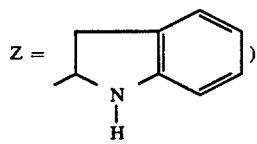

2.9 g of N-[4-(4-methoxyphenyl)-2-thiazolyl]-1-tert-butoxycarbonyl-indoline-2-carboxamide are dissolved in 200 ml of ethyl acetate and 50 ml of a 5N solution of anhydrous HCl in ethyl acetate are added dropwise. The mixture is stirred at ambient temperature for 2 hours. The solid obtained is separated off by filtration and washed with diethyl ether. The dihydrochloride of the final product, which melts at 214° C., is thus isolated in 75% yield.

Salt: $^1$H NMR (250 MHz, DMSOd6) δ(ppm): 3.2–3.7(m,2H); 3.8(s,3H); 5.0(m,1H); 6.0(s,1H); 6.7–7.9(m,9H); 12.1(s,1H).

The examples in Table V were prepared by applying one of the deprotection processes described in Examples 60 and 61 to the corresponding indolines substituted on N by COOC(CH$_3$)$_3$.

TABLE V

Formula I Z = 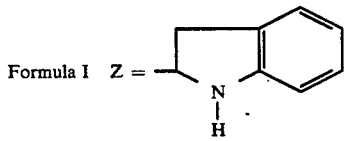

| Ex. | R$_1$ | R$_2$ | R$_3$ | m.p. °C. (salt) | Yield |
|---|---|---|---|---|---|
| 62 | H | H | —⟨C$_6$H$_4$⟩—CH$_3$ | 177 | 61% |
| 63 | H | H | 3,5-dimethylpyridin-4-yl | 200 (HCl) | 46% |
| 64 | H | H | —⟨C$_6$H$_4$⟩—Cl | 185 | 91% |
| 65 | H | H | 2,6-dichlorophenyl | 240 | 78% |
| 66 | H | H | 3,4-dichlorophenyl | 178 | 71% |
| 67 | H | CH$_3$ | —C$_6$H$_5$ | 180 | 60% |
| 68 | H | | —CH$_2$—CH$_2$—C$_6$H$_5$ | 174 | 85% |

TABLE V-continued

Formula I  Z = [2,3-dihydro-1H-indol-2-yl (indoline)]

| Ex. | R$_1$ | R$_2$ | R$_3$ | m.p. °C. (salt) | Yield |
|---|---|---|---|---|---|
| 69 | H | | —CH$_2$—CH$_2$—CH$_2$—(2-methylphenyl) | 182 | 80% |
| 70 | H | | —CH$_2$—CH$_2$—CH$_2$—(2,4,5-trimethylphenyl) | 190 | 72% |
| 71 | H | H | cyclohexyl | 150 | 53% |
| 72 | H | H | 2,4,6-trimethoxyphenyl (3,5-H$_3$CO, 4-OCH$_3$) | 210 | 90% |
| 73 | H | H | 4-methoxyphenyl | 214 (HCl) | 75% |
| 74 | H | H | 2-methoxyphenyl | 163 | 89% |
| 75 | H | H | 2,4-dimethoxyphenyl | 140 | 63% |
| 76 | H | H | 2,6-dimethoxyphenyl | 210 | 79% |
| 77 | H | H | 2,6-dimethyl-4-methoxyphenyl | 134 | 83% |

TABLE V-continued

Formula I  Z = [2,3-dihydro-1H-indol-2-yl]

| Ex. | R₁ | R₂ | R₃ | m.p. °C. (salt) | Yield |
|---|---|---|---|---|---|
| 78 | H | H | 2,4,6-tris(isopropyl)phenyl [(H₃C)₂HC, CH(CH₃)₂, (H₃C)₂HC] | 172 | 80% |
| 79 | CH₃ | H | 2,4,6-trimethylphenyl (H₃C, CH₃, H₃C) | 176 | 65% |
| 80 | H | H | 3,4,5-trimethoxyphenyl (OCH₃, OCH₃, OCH₃) | 120 | 75% |
| 81 | H | CH₃ | 2,5-dimethylphenyl (H₃C, CH₃) | 157 | 82% |
| 82 | H | CH₃ | 4-methoxyphenyl (OCH₃) | 166 | 75% |
| 83 | CH₃ | CH₃ | 2,4,6-trimethoxyphenyl (H₃CO, OCH₃, H₃CO) | 230 | 80% |
| 84 | H | CH₃ | 4-chlorophenyl (Cl) | 150(HCl) | 82% |
| 85 | H | H | 2,5-dimethylphenyl (H₃C, CH₃) | 160(HCl) | 77% |

TABLE V-continued

Formula I   Z = 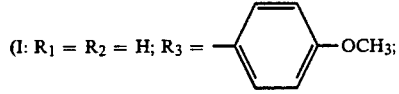

| Ex. | R₁ | R₂ | R₃ | m.p. °C. (salt) | Yield |
|---|---|---|---|---|---|
| 86 | H | H | 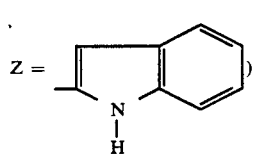 | 262(HCl) | 74% |

EXAMPLE 87

N-[4-(4-Methoxyphenyl)-2-thiazolyl]indole-2-carboxamide (I: R₁ = R₂ = H; R₃ = 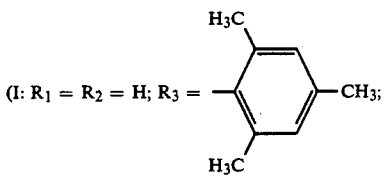

Z = 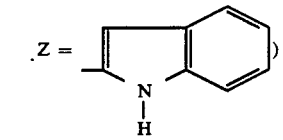)

a) Action of Pd/C/cyclohexene 0.5 g of N-[4-(4-methoxyphenyl)-2-thiazolyl]-indoline-2-carboxamide is dissolved in 50 ml of diphenyl ether and then 0.3 g of 10% Pd-on-charcoal and then 2 ml of cyclohexene are added to the reaction mixture and the reaction mixture is maintained at 160° C. for 5 hours. The catalyst is filtered off hot and washed with dimethylformamide. The filtrates are concentrated and the residue obtained is purified by chromatography on a silica column (eluant: dichloromethane).

Yield: 50%. m.p.=252° C.

$^1$H NMR: (250 MHz,DMSOd6) δ(ppm): 3.8(s,3H); 7.0–7.9(m,10H); 11.9(s,1H); 12.1(s,1H).

b) Oxidation with chloranil (or 2,3,5,6-tetrachloro-1,4-benzoquinone)

0.2 g of N-[2-(4-methoxythiazolyl)]indoline-2-carboxamide is dissolved in 20 ml of xylene, 0.2 g of chloranil is then added and the reaction mixture is refluxed for 3 hours. The solvent is then evaporated and the residue is redissolved in dichloromethane. The organic solution is washed successively with a 1N aqueous sodium hydroxide solution and then with water and dried over anhydrous magnesium sulphate. The residue obtained after evaporation of the solvent is solidified by triturating with diethyl ether and washed abundantly with ethyl ether.

Off-white crystals. Yield: 60%. m.p.=252° C.

EXAMPLE 88

N-[4-(2,4,6-Trimethylphenyl)-2-thiazlyl]indole-2-carboxamide (I: R₁ = R₂ = H; R₃ =

.Z = )

6 g of N-[4-(2,4,6-trimethylphenyl)-2-thiazolyl]-indoline-2-carboxamide are dissolved in 50 ml of 1,2-dimethoxyethane and 4.1 g of 2,3-dichloro-5,6-dicyanobenzoquinone (DDQ) are added. The mixture is stirred at ambient temperature for 3 hours. The reaction mixture is evaporated to dryness and the residue is taken up in ethyl acetate. The organic solution is washed successively with a 1N aqueous sodium hydroxide solution and then with water saturated with NaCL and dried over anhydrous magnesium sulphate. The residue obtained after evaporation of the solvent is triturated with diisopropyl ether and the solid is washed abundantly with this solvent. Whitish crystals are isolated.

Yield: 82%. m.p.=265° C.

$^1$H NMR: (250 MHz,DMSOd6) δ(ppm): 2.07(s,6H); 2.69(s,3H); 6.92–7.69(m,8H); 11.92(s,1H); 12.77(s,1H).

The products of formula I in which Z represents

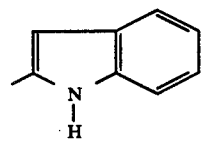

which are described in Table VI were prepared from indolines by applying one of the processes of Examples 87 and 88.

TABLE VI

| Ex. | R₁ | R₂ | R₃ | m.p. °C. | Yield |
|---|---|---|---|---|---|
| 89 | H | H | 4-methylphenyl | 265 | 58% |
| 90 | H | H | 3,5-dimethylpyridin-4-yl | 320 | 14% |
| 91 | H | H | 4-chlorophenyl | 278 | 40% |
| 92 | H | H | 2,6-dichlorophenyl | 275 | 72% |
| 93 | H | H | 3,4-dichlorophenyl | 286 | 33% |
| 94 | H | CH₃ | phenyl | 220 | 52% |
| 95 | H | | —CH₂—CH₂—(2-methylphenyl) | 283 | 45% |
| 96 | H | | —CH₂—CH₂—CH₂—(2-methylphenyl) | 276 | 70% |
| 97 | H | | —CH₂—CH₂—CH₂—(2,4,5-trimethylphenyl) | 270 | 50% |
| 98 | H | H | cyclohexyl | 233 | 61% |
| 99 | H | H | 2,4,6-trimethoxyphenyl | 270 | 78% |

TABLE VI-continued

| Ex. | R₁ | R₂ | R₃ | m.p. °C. | Yield |
|---|---|---|---|---|---|
| 100 | H | H | 2-methoxyphenyl (H₃CO-) | 250 | 79% |
| 101 | H | H | 2,4-dimethoxyphenyl (H₃CO-, -OCH₃) | 252 | 75% |
| 102 | H | H | 2,6-dimethoxyphenyl (H₃CO-, H₃CO-) | 250 (HCl) | 90% |
| 103 | H | H | 2-methoxy-4,5-dimethylphenyl (H₃CO-, -CH₃, H₃C-) | 260 | 73% |
| 104 | H | H | 2,6-diisopropyl-4-isopropylphenyl ((H₃C)₂CH-, -CH(CH₃)₂, (H₃C)₂HC-) | 262 (HCl) | 75% |
| 105 | H | H | 3,4,5-trimethoxyphenyl (-OCH₃, -OCH₃, -OCH₃) | 215 | 72% |
| 106 | H | CH₃ | 2,4-dimethylphenyl (H₃C-, -CH₃) | 283 | 76% |
| 107 | H | CH₃ | 4-methoxyphenyl (-OCH₃) | 250 | 80% |
| 108 | H | CH₃ | 4-chlorophenyl (-Cl) | 278 | 75% |
| 109 | H | H | 2,4-dimethylphenyl (H₃C-, -CH₃) | 231 | 69% |

The following examples relate to compounds of formula I in which

Z = 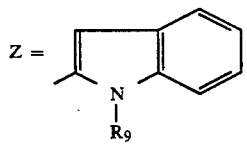

EXAMPLE 110

Methyl 2-[4-(2,4,6-trimethylphenyl)-2-thiazolyl]aminocarbonyl-1-indolyl acetate (I: $R_1=R_2=H$; $R_3=2,4,6-(CH_3)_3C_6H_2$; $R_9=CH_2COOCH_3$)

1.34 g of 1-methoxycarbonylmethylindole-2-carboxylic acid, 1.9 g of triethylamine and 2.7 g of benzotriazolyloxytris(dimethylamino)phosphonium hexafluorophosphate (BOP) are added successively to a solution of 1.7 g of 4-(2,4,6-trimethylphenyl)-2-aminothiazole hydrobromide in 30 ml of dimethylformamide. The reaction mixture is stirred overnight at about 20° C. and is then poured into a volume of ice-water before extracting with ethyl acetate. The dried organic extracts are evaporated to dryness and the residue is recrystallised from ethyl acetate. m.p.=206° C., yield: 82%.

EXAMPLE 111

2-[4-(2,4,6-Trimethylphenyl)-2-thiazolyl]aminocarbonyl-1-indolylacetic acid (I: $R_1=R_2=H$; $R_3=2,4,6-(CH_3)_3C_6H_2$; $R_9=CH_2COOH$)

1g of the ester obtained in Example 1 is dissolved in 15 ml of methanol and 1.8 ml of a 2N aqueous sodium hydroxide solution are introduced into the mixture; after stirring at about 20° C. for 3 hours, the mixture is brought to 60° C. for one hour, the solvent is then removed and the residue is taken up in 15 ml of water. The aqueous solution is acidified to pH=4 by addition of an aqueous hydrochloric acid solution; the precipitate formed is isolated by filtration. m.p.=244° C., yield 81%.

EXAMPLE 112

N-[4-(2,4,6-Trimethylphenyl)-2-thiazolyl]-1-(2-tetrahydropyranyl)indole-2-carboxamide (I: $R_1 = R_2 = H$; 2,4,6-$(CH_3)_3C_6H_2$; $R_9 =$ 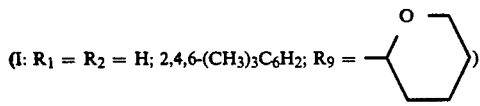)

2.45 g of triethylamine, 2 g of 1-(2-tetrahydropyranyl)indole-2-carboxylic acid and 3.6 g of BOP are introduced successively into a solution of 2.44 g of 4-(2,4,6-trimethylphenyl)-2-aminothiazolehydrobromide in 30 ml of dimethylformamide. After stirring for 12 hours at about 20° C., the reaction mixture is poured into a volume of ice-water. The precipitate formed is isolated by filtration and recrystallised from ethanol m.p.=188° C., yield 80%.

EXAMPLE 113

N-[4-(2,4,6-trimethylphenyl)-2-thiazolyl]indole-2-carboxamide (I: $R_1=R_2=R_9=H$; $R_3=2,4,6-(CH_3)_3C_6H_2$)

A solution of 1 g of the compound obtained according to Example 112 in 50 ml of the methanol and 5 ml of a 6N aqueous hydrochloric acid solution is kept at 60° C. for 4 hours. After returning to about 20° C., the precipitate formed is isolated. m.p.=265° C., yield 95%.

EXAMPLE 114

N-[4-(2,4,6-trimethylphenyl)-2-thiazolyl]-1-[2-(dimethylamino)ethyl]indole-2-carboxamide (I: $R_1=R_2=H$; $R_3=2,4,6-(CH_3)_3C_6H_2$; $R_9=(CH_2)_2N(CH_3)_2$)

3.86 g of 4-(2,4,6-trimethylphenyl)-2-aminothiazole hydrobromide, 2.59 g of triethylamine and 5.7 g of BOP are added successively to a solution of 3 g of 1-[2-(N,N-dimethylamino)ethyl]indole-2-carboxylic acid in 75 ml of dimethylformamide. The reaction mixture is stirred at ambient temperature overnight and is poured into a volume of ice-water before extracting with ethyl acetate. After drying, the organic extract is evaporated to dryness. The solid obtained is recrystallised from ethyl acetate. m.p.=100° C., yield: 72%.

The hydrochloride is prepared in ethanol by the action of HCl. Hydrochloride, m.p. 270° C.

The products of formula I in which

Z = 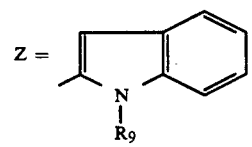

described in Table VII were prepared by applying one of the method of Examples 110 to 114.

TABLE VII

| Ex. | $R_1$ | $R_2$ | $R_3$ | $R_9$ | m.p. °C. | Yield % |
|---|---|---|---|---|---|---|
| 115 | H | H | 2,4,6-(CH₃)₃C₆H₂ (H₃C, CH₃, H₃C) | —(CH₂)₃N(CH₃)₂ | 258(HCl) | 68 |

TABLE VII-continued

| | | | | | | |
|---|---|---|---|---|---|---|
| 116 | H | H | 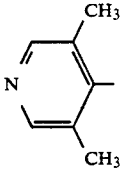 3,4,5-trimethylpyridyl | —(CH$_2$)$_2$N(CH$_3$)$_2$ | 288(HCl) | 72 |
| 117 | H | H | 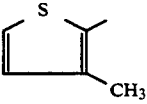 2,3-dimethylthienyl | —(CH$_2$)$_2$N(CH$_3$)$_2$ | 168 | 69 |
| 118 | H | CH$_3$ | 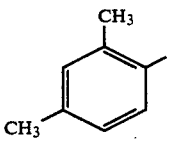 2,4-dimethylphenyl | —(CH$_2$)$_2$N(CH$_3$)$_2$ | 274(HCl) | 75 |
| 119 | H | H | 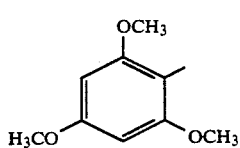 2,4,6-trimethoxyphenyl | —(CH$_2$)$_2$N(CH$_3$)$_2$ | 218(HCl) | 80 |
| 120 | H | H | 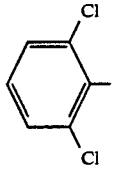 2,6-dichlorophenyl | —(CH$_2$)$_2$N(CH$_3$)$_2$ | 258(HCl) | 78 |
| 121 | —(CH$_2$)$_2$N(CH$_3$)$_2$ | H | 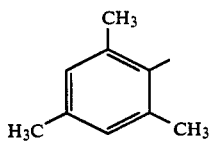 2,4,6-trimethylphenyl | —(CH$_2$)$_2$N(CH$_3$)$_2$ | 180(HCl) | 70 |
| 122 | —(CH$_2$)$_2$N(CH$_3$)$_2$ | H | 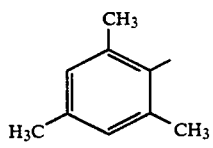 2,4,6-trimethylphenyl | H | 185 | 71 |
| 123 | H | H | 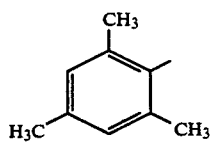 2,4,6-trimethylphenyl | —CH$_2$COOCH$_3$ | 206 | 82 |
| 124 | H | H | 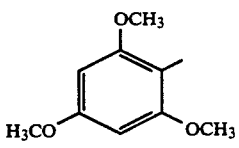 2,4,6-trimethoxyphenyl | —CH$_2$COOCH$_3$ | 186 | 77 |
| 125 | H | H | 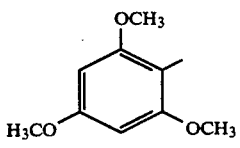 2,4,6-trimethoxyphenyl | —CH$_2$COOH | 232 | 62 |

TABLE VII-continued
| | | | | | | |
|---|---|---|---|---|---|---|
| 126 | H | H | 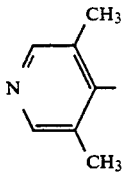 3,5-dimethylpyridin-4-yl | —CH₂COOCH₃ | 230(HCl) | 60 |
| 127 | H | H | 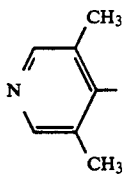 3,5-dimethylpyridin-4-yl | —CH₂COOH | 222 | 65 |
| 128 | H | H | 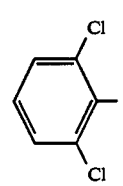 2,6-dichlorophenyl | —CH₂COOCH₃ | 130 | 62 |
| 129 | H | H | 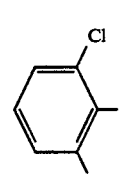 2,6-dichlorophenyl | —CH₂COOH | 255 | 63 |
| 130 | H | H | 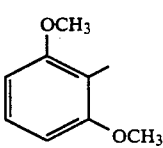 2,6-dimethoxyphenyl | —CH₂COOCH₃ | 188 | 78 |
| 131 | H | H | 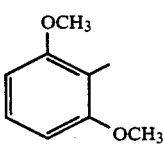 2,6-dimethoxyphenyl | —CH₂COOH | 238 | 80 |
| 132 | H | H | 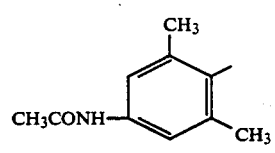 4-acetamido-2,6-dimethylphenyl | —CH₂COOCH₃ | 272 | 74 |
| 133 | H | H | 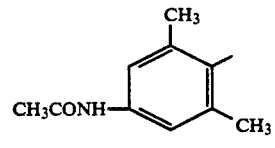 4-acetamido-2,6-dimethylphenyl | —CH₂COOH | 209 | 93 |
| 134 | H | H | 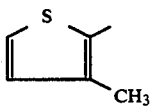 3-methylthien-2-yl | —CH₂COOCH₃ | 183 | 74 |
| 135 | H | H | 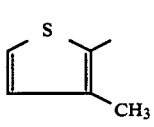 3-methylthien-2-yl | —CH₂COOH | 212 | 83 |

TABLE VII-continued

| | | | | | m.p. °C. | Yield % |
|---|---|---|---|---|---|---|
| 136 | H | H | 2-methylphenyl (o-tolyl) | —CH₂COOCH₃ | 145 | 61 |
| 137 | H | H | 2-methylphenyl (o-tolyl) | —CH₂COOH | 172 | 80 |
| 138 | H | H | 2,4,6-trimethylphenyl (mesityl) | —(CH₂)₂OCH₃ | 170 | 74 |
| 139 | H | H | 2,4,6-trimethylphenyl (mesityl) | tetrahydropyran-2-yl | 188 | 80 |

| Ex. | R₁ | R₂ | R₃ | R₉ | m.p. °C. (salt) | Yield % |
|---|---|---|---|---|---|---|
| 140 | H | H | 2,4,6-trimethylphenyl | CHCH₃COOCH₃ | 142 | 78 |
| 141 | H | H | 2,4,6-trimethylphenyl | CH₂CONH₂ | 286 | 82 |
| 142 | H | H | 3-methoxy-2,5-dimethylphenyl (with H₃C substituent) | tetrahydropyran-2-yl | 181 | 80 |
| 143 | H | H | 2,4,6-trimethylphenyl | CH₂CH₂OH | 180 | 90 |
| 144 | H | H | 1-methylpyrrol-2-yl | tetrahydropyran-2-yl | 180 | 79 |

TABLE VII-continued

| | | | | | | |
|---|---|---|---|---|---|---|
| 145 | CH₃ | H | 2,4,6-(H₃CO)₃-3-CH₃-phenyl (H₃CO, OCH₃, H₃CO with CH₃) | CH₂COOCH₃ | 157 | 81 |
| 146 | H | H | 2,6-(H₃C)₂-phenyl | CH₂COOH | 253 (HCl) | 78 |
| 147 | H | H | 2,6-(H₃C)₂-phenyl | CH₂COOCH₃ | 196 | 89 |
| 148 | H | H | 2,4,6-(H₃C)₃-phenyl | CHCH₃COOH | 188 | 87 |
| 149 | H | H | 2,4,6-(H₃C)₃-phenyl | CH₂CH₂CN | 230 | 78 |
| 150 | H | H | 2,6-(H₃C)₂-phenyl | tetrahydropyran-2-yl | 183 | 80 |
| 151 | H | H | 2-Cl-phenyl | CH₂COOCH₃ | 184 | 80 |
| 152 | H | H | 2-Cl-phenyl | CH₂COOH | 197 | 76 |

Other examples of compounds of formula I are shown in the following Table VIII:

TABLE VIII

| Ex. | R₁ | R₂ | R₃ | Z | m.p. °C.(salt) |
|---|---|---|---|---|---|
| 153 | H | H | 2,4,5-trimethoxyphenyl (H₃CO, OCH₃, H₃CO) | 5-methoxy-2-methyl-1-(CH₂COOC(CH₃)₃)-indol-3-yl | 120 |
| 154 | H | H | 2,4,5-triethoxyphenyl (H₅C₂O, OC₂H₅, H₅C₂O) | 5-methoxy-2-methyl-1-(CH₂COOC(CH₃)₂)-indol-3-yl | 122 |
| 155 | H | H | 2,4,5-triethoxyphenyl (H₅C₂O, OC₂H₅, H₅C₂O) | 5-methoxy-2-methyl-1-(CH₂COOH)-indol-3-yl | 210 |
| 156 | H | H | 2,4,5-trimethoxyphenyl (H₃CO, OCH₃, H₃CO) | 2-methyl-7-amino-indol-3-yl | >250 |
| 157 | H | H | 2,4,5-trimethoxyphenyl (H₃CO, OCH₃, H₃CO) | 2-methyl-5-methoxy-6-benzyloxy-indol-3-yl | 238 |
| 158 | H | H | 2,4,5-trimethoxyphenyl (H₃CO, OCH₃, H₃CO) | 2-methyl-7-nitro-indol-3-yl | >250 |
| 159 | H | H | 2,4,5-triethylphenyl (H₅C₂, C₂H₅, H₅C₂) | 2-methyl-indol-3-yl | >260 |
| 160 | H | H | 2,4,5-trimethylphenyl (H₃C, CH₃, H₃C) | 2-methyl-indol-3-yl | 257(HCl) |
| 161 | H | H | 2,4,5-trimethylphenyl (H₃C, CH₃, H₃C) | 5-methoxy-2-methyl-indol-3-yl | 240(HCl) |

TABLE VIII-continued

| Ex. | R₁ | R₂ | R₃ | Z | m.p. °C.(salt) |
|---|---|---|---|---|---|
| 162 | H | H | 3,5-dimethylphenyl (H₃C, CH₃, H₃C) | 5-chloro-2-methylindol-yl | 310 |
| 163 | H | H | 2-chlorophenyl | 2-methylindol-yl | 249(HCl) |
| 164 | H | H | 2-methylphenyl | 2-methylindol-yl | 223 |
| 165 | H | H | 2-trifluoromethylphenyl | 2-methylindol-yl | 203 |
| 166 | H | H | 4-cyclohexylphenyl | 2-methylindol-yl | 165 |
| 167 | H | CH₃ | 4-methylphenyl | 2-methylindol-yl | 280 |
| 168 | H | H | 3,5-dimethylphenyl | 2-methylbenzofuran-yl | 173 |

The nuclear magnetic resonance spectra of the compounds of the preceding examples were recorded. The chemical shifts observed are indicated in Table IX, specifying the frequency applied and the solvent.

TABLE IX

| EXAMPLES | δ(ppm) |
|---|---|
| 3 | (80MHz, DMSOd6): 2.1(s, 6H); 2.3(s, 3H); 7.0-8.2(m, 7H); 9.2(d, 1H); 9.6(d, 1H); 13.1(s, 1H). |
| 4 | (80MHz, DMSOd6): 2.2(s, 6H); 2.3(s, 3H); 4.2(s, 3H); 7.0-7.9(m, 8H); 12.8(s, 1H). |
| 5 | (250MHz, DMSOd6): 2.0(s, 6H); 2.2(s, 3H); 6.9-8.6(m, 8H); 11.9(s, 1H); 12.3(s, 1H). |
| 6 | (80MHz, CDCl₃): 2.1(s, 6H); 2.4(s, 3H); 6.8-8.4(m, 9H); 11.5(s, 1H). |
| 7 | (80MHz, DMSOd6): 2.2(s, 6H); 2.5(s, 3H); 7.0(s, 2H); 7.3(s, 1H); 7.9-8.4(m, 6H); 12.7(s, 1H). |
| 8 | (80MHz, DMSOd6): 2.4(s, 3H); 7.3-8.3(m, 9H); 9.5(s, 1H); 9.6(s, 1H); 13.0(s, 1H). |

TABLE IX-continued

| EXAMPLES | δ(ppm) |
|---|---|
| 9 | (250MHz, DMSOd6): 3.0(m, 4H); 7.1–9.4(m, 10H); 13.0(s, 1H). |
| 10 | (250MHz, DMSOd6): 2.9–3.1(m, 4H); 4.1(s, 3H); 7.1–7.9 (m, 9H); 12.7(s, 1H). |
| 11 | (80MHz, DMSOd6): 2.1–3.5(m, 6H); 7.2–9.4(m, 10H); 13.0(s, 1H). |
| 12 | (250MHz, DMSOd6): 2.1–3.0(m, 6H); 7.1–8.0(m, 9H); 11.9(s, 1H); 12.7(s, 1H). |
| 13 | (250MHz, DMSOd6): 2.1–3.0(m, 6H); 4.1(s, 3H); 7.0–7.8(m, 9H); 12.7(s, 1H). |
| 14 | (80MHz, DMSOd6): 3.7(s, 6H); 3.9(s, 3H); 6.3(s, 2H); 7.1(s, 1H); 7.7–8.3(m, 4H); 9.3(d, 1H); 9.7(d, 1H); 13.0(s, 1H). |
| 15 | (250MHz, DMSOd6): 3.7(s, 6H); 3.9(s, 3H); 4.1(s, 3H); 6.3(s, 2H); 6.9(s, 1H); 7.1–7.7(m, 5H); 12.7(s, 1H). |
| 16 | (250MHz, DMSOd6): 3.8(s, 3H); 7.0–9.4(m, 11H); 12.7(s, 1H). |
| 17 | (80MHz, DMSOd6): 7.2–9.6(m, 11H); 13.0(s, 1H). |
| 18 | (250MHz, DMSOd6): 1.1(d, 12H); 1.3(d, 6H); 2.6(m, 2H); 2.9(m, 1H); 4.1(s, 3H); 7–7.7(m, 8H); 12.7(s, 1H). |
| 19 | (250MHz, DMSOd6): 2.0(s, 6H); 5.8(s, 2H); 7.3(s, 1H); 7.7–8.3(m, 4H); 9.2(s, 1H); 9.4(s, 1H); 13.1(s, 1H). |
| 20 | (200MHz, DMSOd6): 1.40(s, 9H); 3.60(s, 6H); 3.80(s, 3H); 6.20(s, 2H); 6.80(s, 1H); 7.10(s, 1H); 7.20(t, 1H); 7.40(t, 1H); 7.60(d, 1H); 8.00(d, 1H); 12.05(s, 1H). |
| 21 | (200MHz, DMSOd6): 1.20(2t, 9H); 4.00(m, 6H); 5.20(s, 2H); 6.20(s, 2H); de7.0 & 7.80(m, 10H); 8.10(d, 1H). 12.10(s, 1H). |
| 22 | (200MHz, DMSOd6): 2.60(s, 3H); 2.90(m, 4H); 3.80(s, 3H); 3.75(s, 3H); 6.65(s, 2H); 7.15(s, 2H); 7.40(t, 1H); 7.50 (d, 1H); 8.05(d, 1H); 12.80(s, 1H). |
| 23 | (200MHz, DMSOd6): 1.23(t, 3H); 2.60(m, 5H); 3.68(s, 6H); 6.60(s, 2H); 7.00(s, 1H); 7.20(m, 3H); 7.80(d, 1H); 8.05 (d, 1H); 13.00(s, 1H). |
| 24 | (200MHz, DMSOd6): 2.70(s, 3H); 3.68(s, 6H); 3.80(s, 3H); 6.30(s, 2H); 6.90(s, 1H); 7.40(m, 1H); 8.40(m, 2H); 9.00(s, 1H); 12.30(s, 1H). |
| 25 | (200MHz, DMSOd6): 2.80(s, 3H); 3.70(s, 6H); 3.90(s, 3H); 6.30(s, 2H); 7.00(s, 1H); 7.40(m, 3H); 7.80(d, 1H); 8.10 (d, 1H); 13.00(m, 1H). |
| 26 | (200MHz, DMSOd6): 3.60(s, 6H); 3.80(s, 3H); 6.20(s, 2H); 6.95(s, 1H); 7.30(t, 1H); 7.45(t, 1H); 7.70(d, 1H); 7.80 (d, 1H); 8.00(s, 1H); 12.80(s, 1H). |
| 27 | (200MHz, DMSOd6): 2.60(s, 3H); 3.62(s, 6H); 3.80(s, 3H); 6.25(s, 2H); 6.95(s, 1H); 7.30(t, 1H); 7.42(t, 1H); 7.58 (d, 1H); 7.80(d, 1H); 12.60(s, 1H). |
| 28 | (200MHz, DMSOd6): 3.72(s, 6H); 3.81(s, 3H); 6.30(s, 2H); 7.00(s, 1H); 7.80(d, 1H); 8.30(d, 1H); 8.70(s, 1H); 12.00 (s, 1H). |
| 29 | (200MHz, DMSOd6): 3.68(s, 6H); 3.82(s, 3H); 6.15(s, 2H); 7.00(s, 1H); 7.80(d, 1H); 8.20(d, 1H); 8.95(s, 1H); 12.10 (s, 1H). |
| 30 | (200MHz, DMSOd6): 3.65(s, 6H); 3.80(s, 3H); 6.05(m, 2H); 7.60(s, 1H); 7.80(d, 1H); 8.20(d, 1H); 8.60(s, 1H); 9.50 (s, 1H); 12.60(s, 1H); 13.10(s, 1H). |
| 31 | (200MHz, DMSOd6): 3.70(s, 6H); 6.20(s, 2H); 7.05(s, 1H); 7.80(d, 1H); 8.40(d, 1H); 8.80(s, 1H); 9.50(s, 1H); 11.00 (s, 1H); 12.60(s, 1H). |
| 32 | (200MHz, DMSOd6): 1.20(t, 3H); 2.60(q, 2H); 3.72(s, 6H); 6.60(s, 2H); 7.05(m, 2H); 7.23(t, 1H); 7.32(d, 1H); 7.70 (m, 2H); 11.50(s, 1H); 12.60(s, 1H). |
| 33 | (200MHz, DMSOd6): 1.12(t, 6H); 1.30(t, 3H); 3.90(q, 4H); 4.00(q, 2H); 6.20(s, 2H); 6.90(s, 1H); 7.00(t, 1H); 7.20 (t, 1H); 7.40(d, 1H); 7.60(m, 2H); 11.80(s, 1H); 12.20 (s, 1H). |
| 34 | (200MHz, DMSOd6): 2.70(m, 4H); 3.65(s, 6H); 6.80(m, 2H); 6.85(m, 2H); 7.00(t, 1H); 7.30(d, 1H); 7.46(d, 1H); 11.50 (s, 1H). |
| 80 | (200MHz, DMSOd6): 3.15(m, 1H); 3.35(m, 1H); 3.69(s, 3H); 3.84(s, 6H); 4.66(m, 1H); 6.66–7.72(m, 8H); 12.35(m, 1H). |
| 81 | (200MHz, DMSOd6): 2.14(s, 3H); 2.17(s, 3H); 2.31(s, 3H); 3.15(m, 1H); 3.35(m, 1H); 4.55(m, 1H); 6.05(m, 1H); 6.57–7.11(m, 7H); 11.95(s, 1H). |
| 82 | (250MHz, DMSOd6): 2.43(s, 3H); 3.15(m, 1H); 3.35(m, 1H); 3.79(s, 3H); 4.55(m, 1H); 6.01(d, 1H); 6.54–7.95(m, 8H); 11.95(s, 1H). |
| 83 | (200MHz, DMSOd6): 3.15–3.40(m, 2H); 3.66(s, 6H); 3.67(s, 3H); 3.82(s, 3H); 5.05(m, 1H); 6.05(m, 1H); 6.29(s, 2H); 6.57–6.62(m, 2H); 6.92–7.03(m, 3H). |
| 84 | (200MHz, DMSOd6): 2.51(s, 3H); 3.15(m, 1H); 3.35(m, 1H); 4.65(m, 1H); 6.84–7.70(m, 9H); 11.85(s, 1H). |

TABLE IX-continued

| EXAMPLES | δ(ppm) |
|---|---|
| 85 | (250MHz, DMSOd6): 2.91(s, 3H); 2.50(s, 3H); 3.30(m, 1H); 3.55(m, 1H); 4.90(m, 1H); 7.04–7.49(m, 9H); 10.55(m, 2H). |
| 86 | (250MHz, DMSOd6): 1.15(s, 12H); 1.25(s, 6H); 2.55(m, 2H); 2.80(m, 1H); 3.15–3.35(m, 2H); 4.55(m, 1H); 6.05(s, 1H); 6.65–7.45(m, 8H); 12.25(s, 1H). |
| 89 | (250MHz, DMSOd6): 2.3(s, 3H); 7.1–7.9(m, 10H); 11.9(s, 1H); 12.8(s, 1H). |
| 90 | (250MHz, DMSOd6): 2.3(s, 6H); 6.4–8.5(m, 8H); 12.0(s, 1H); 12.7(s, 1H). |
| 91 | (250MHz, DMSOd6): 7.0(m, 10H); 11.9(s, 1H); 12.8(s, 1H). |
| 92 | (250MHz, DMSOd6): 7.0–7.8(m, 9H); 11.9(s, 1H); 12.8(s, 1H). |
| 93 | (250MHz, DMSOd6): 7.0–8.2(m, 9H); 11.8(s, 1H); 12.7(s, 1H). |
| 94 | (250MHz, DMSOd6): 2.5(s, 3H); 7.0–7.9(m, 10H); 11.8(s, 1H); 12.7(s, 1H). |
| 95 | (250MHz, DMSOd6): 2.8–3.1(m, 4H); 7.0–8.0(m, 9H); 12.1(s, 1H); 13.0(s, 1H). |
| 97 | (250MHz, DMSOd6): 2.0–3.0(m, 6H); 6.9–7.9(m, 7H); 11.9(s, 1H); 12.5(s, 1H). |
| 98 | (250MHz, DMSOd6): 1.2–2.6(m, 1H); 6.7(s, 1H); 7.0–7.7(m, 5H); 11.7(s, 1H); 12.7(s, 1H). |
| 99 | (250MHz, DMSOd6): 3.7(s, 6H); 3.8(s, 3H); 6.3(s, 2H); 6.9–7.8(m, 6H); 11.8(s, 1H); 12.7(s, 1H). |
| 100 | (250MHz, DMSOd6): 3.9(s, 3H); 7.0–8.2(m, 10H); 11.8(s, 1H); 12.7(s, 1H). |
| 101 | (250MHz, DMSOd6): 3.6(s, 3H); 3.9(s, 3H); 6.7–8.1(m, 9H); 11.7(s, 1H); 12.7(s, 1H). |
| 102 | (250MHz, DMSOd6): 3.7(s, 6H); 6.8–7.8(m, 9H); 11.9(s, 1H); 12.7(s, 1H). |
| 103 | (250MHz, DMSOd6): 2.1(s, 3H); 2.3(s, 3H); 3.6(s, 3H); 6.7–7.6(m, 8H); 11.9(s, 1H); 12.7(s, 1H). |
| 104 | (250MHz, DMSOd6): 1.1(d, 12H); 1.3(d, 6H); 2.6(m, 2H); 2.9(m, 1H); 7.1–7.7(m, 8H); 11.9(s, 1H); 12.7(s, 1H). |
| 105 | (200MHz, DMSOd6): 3.71(s, 3H); 3.87(s, 6H); 7.06–7.71 (m, 8H); 11.93(s, 1H); 12.79(s, 1H). |
| 106 | (200MHz, DMSOd6): 2.18(s, 3H); 2.21(s, 3H); 2.32(s, 3H); 7.04–7.69(m, 8H); 11.90(s, 1H); 12.59(s, 1H). |
| 107 | (200MHz, DMSOd6): 2.49(s, 3H); 3.81(s, 3H); 7.016–7.68 (m, 9H); 11.91(s, 1H); 12.65(s, 1H). |
| 108 | (200MHz, DMSOd6): 2.51(s, 3H); 7.26–7.74(m, 9H); 11.92 (s, 1H); 12.71(s, 1H). |
| 109 | (200MHz, DMSOd6): 2.31(s, 3H); 2.44(s, 3H); 7.06–7.70 (m, 9H); 11.92(s, 1H); 12.77(s, 1H). |
| 111 | (200MHz, DMSOd6): 2.1(s, 6H); 2.3(s, 3H); 5.4(s, 2H); 6.9–7.9(m, 8H); 12.9(s, 2H). |
| 112 | (200MHz, DMSOd6): 1.5–2.4(m, 6H); 2.1(s, 6H); 2.3(s, 3H); 12.8(s, 1H). |
| 113 | (250MHz, DMSOd6): 2.1(s, 6H); 2.3(s, 3H); 6.7–7.7(m, 8H); 11.8(s, 1H); 12.7(s, 1H). |
| 114 | (200MHz, DMSOd6): 2.1(s, 6H); 2.2(s, 6H); 2.3(s, 3H); 2.6(t, 2H); 4.7(t, 2H); 6.9–7.6(m, 8H). |
| 115 | (200MHz, DMSOd6): 2.07(s, 6H); 2.27(m, 5H); 2.75(d, 6H); 3.16(t, 2H); 4.72(t, 2H); 6.93(s, 2H); 7.06–7.77(m, 6H); 10.75(m, 1H); 12.9(m, 1H). |
| 116 | (200MHz, DMSOd6): 2.31(s, 6H); 2.90(s, 6H); 3.48(t, 2H); 4.95(t, 2H); 7.21–7.76(m, 3H); 8.68(s, 2H); 11.43(m, 1H); 13.00(m, 1H). |
| 117 | (200MHz, DMSOd6): 2.2(s, 6H); 2.4(s, 3H); 2.7(t, 2H); 4.7(t, 2H); 7.0–7.7(m, 8H); 13.4(m, 1H). |
| 118 | (200MHz, DMSOd6): 2.18(d, 6H); 2.32(s, 3H); 2.86(s, 6H); 3.44(t, 2H); 5.06(t, 2H); 7.04–7.95(m, 8H); 11.60(m, 1H). |
| 119 | (200MHz, DMSOd6): 2.88(d, 6H); 3.46(t, 2H); 3.71(s, 6H); 3.81(s, 3H); 5.05(t, 2H); 5.7(m, 1H); 6.32(s, 2H); 7.028–7.91(m, 6H); 11.13(m, 1H). |
| 120 | (200MHz, DMSOd6): 2.23(s, 6H); 2.65(t, 2H); 4.75(t, 2H); 7.11–7.72(m, 9H); 13.00(m, 1H). |
| 121 | (200MHz, DMSOd6): 2.09–5.12(m, 29H); 6.97–7.89(m, 8H); 11.10(m, 1H); 11.47(m, 1H). |
| 122 | (200MHz, DMSOd6): 2.09–2.12(m, 12H); 2.28(s, 3H); 2.70 (t, 2H); 4.59(t, 2H); 6.95–7.65(m, 8H); 12.21(s, 1H). |
| 123 | (200MHz, DMSOd6): 2.1(s, 6H); 2.3(s, 3H); 3.7(s, 3H); 5.5(s, 2H); 6.9–7.8(m, 8H); 12.8(s, 1H). |
| 124 | (200MHz, DMSOd6): 3.69(s, 9H); 3.84(s, 3H); 5.50(s, 2H); 6.30(s, 2H); 6.92–7.75(m, 6H); 12.73(s, 1H). |
| 125 | (200MHz, DMSOd6): 3.69(s, 6H); 3.83(s, 3H); 5.41(s, 2H); 6.30(s, 2H); 6.93–7.74(m, 6H); 12.80(m, 2H). |
| 126 | (200MHz, DMSOd6): 2.35(s, 6H); 3.69(s, 3H); 5.49(s, 2H); 7.63–7.82(m, 8H); 13.0(m, 1H). |
| 127 | (200MHz, DMSOd6): 2.15(s, 6H); 5.35(s, 2H); 7.16–7.74 (m, 6H); 8.37(s, 2H), 13.05(m, 1H). |
| 128 | (200MHz, DMSOd6): 3.70(s, 3H); 5.50(s, 2H); 7.18–7.81 (m, 9H); 12.93(s, 1H). |

TABLE IX-continued

| EXAMPLES | δ(ppm) |
|---|---|
| 129 | (200MHz, DMSOd6): 5.09(s, 2H); 7.09–7.68(m, 9H); 13.70 (m, 1H). |
| 130 | (200MHz, DMSOd6): 3.7(s, 9H); 5.5(s, 2H); 6.7–7.9 (m, 9H); 12.8(s, 1H). |
| 131 | (200MHz, DMSOd6): 3.7(s, 6H); 5.4(s, 2H); 6.7–7.9(m, 9H). |
| 132 | (200MHz, DMSOd6): 2.1(s, 9H); 3.7(s, 3H); 5.5(s, 2H); 7.0–7.8(m, 8H); 9.9(s, 9H); 12.8(s, 1H). |
| 133 | (200MHz, DMSOd6): 2.1(s, 9H); 5.4(s, 2H); 7.1–7.8(m, 8H); 9.9(s, 1H). |
| 134 | (200MHz, DMSOd6): 2.4(s, 3H); 3.7(s, 3H); 5.5(s, 2H); 7.0–7.9(m, 8H); 12.9(s, 1H). |
| 135 | (200MHz, DMSOd6): 2.4(s, 3H); 5.4(m, 2H); 7.0–7.9 (m, 8H); 12.8(m, 2H). |
| 136 | (200MHz, DMSOd6): 2.48(s, 3H); 3.71(s, 3H); 5.51(s, 2H); 7.31–7.85(m, 10H). |
| 137 | (200MHz, DMSOd6): 2.46(s, 3H); 5.38(s, 2H); 7.29–7.79 (m, 9H); 12.83(m, 2H). |
| 138 | (250MHz, DMSOd6): 2.07(s, 6H); 2.26(s, 3H); 3.17(s, 3H); 3.69(t, 2H); 4.80(t, 2H); 6.92(s, 2H); 7.04–7.69(m, 6H); 12.73(s, 1H). |
| 139 | (200MHz, DMSOd6): 1.73–2.27(m, 19H); 2.07(s, 6H); 2.27 (s, 3H); 3.6(s, 1H); 3.78(s, 3H); 4.4(m, 1H); 6.35(m, 1H) 6.93–7.81(m, 7H); 12.8(s, 1H). |
| 140 | (200MHz, DMSOd6): 1.7(d, 3H); 2.1(s, 6H); 2.3(s, 3H); 3.6(s, 3H); 6.1(q, 1H); 6.9–7.5(m, 8H); 12.8(s, 1H). |
| 141 | (200MHz, DMSOd6): 2.1(s, 6H); 2.3(s, 3H); 5.3(s, 2H); 6.9–7.7(m, 8H); 12.7(s, 1H). |
| 142 | (200MHz, DMSOd6): 1.5–2.5(m, 6H); 2.1(s, 3H); 2.3(s, 3H); 3.17(m, 4H); 4.2(m, 1H); 6.4(m, 1H); 6.7–7.9(m, 8H); 12.8(s, 1H). |
| 143 | (200MHz, DMSOd6): 2.1(s, 6H); 2.3(s, 3H); 3.7(t, 2H); 4.7(t, 2H); 6.9–7.7(m, 8H); 12.7(s, 1H). |
| 144 | (200MHz, DMSOd6): 1.5–2.4(m, 6H); 3.7(m, 1H); 3.9(s, 3H); 4.1(m, 1H); 6.1–7.9(m, 10H); 12.8(s, 1H). |
| 145 | (200MHz, DMSOd6): 3.7(s, 9H); 3.84(s, 3H); 3.85(s, 3H); 5.3(s, 2H); 6.3((s, 2H), 7.1–7.8(m, 6H). |
| 146 | (200MHz, DMSOd6): 2.11(s, 6H); 5.40(s, 2H); 7.12–7.76 (m, 9H). |
| 147 | (200MHz, DMSOd6): 2.11(s, 6H); 3.70(s, 3H); 5.50(s, 2H); 7.10–7.14(m, 9H); 12.8(s, 1H). |
| 148 | (200MHz, DMSOd6): 1.7(d, 3H); 2.1(s, 6H); 2.3(s, 3H); 6.1(q, 1H); 6.9–7.7(m, 8H); 12.8(s, 2H). |
| 149 | (200MHz, DMSOd6): 2.1(s, 6H); 2.3(s, 3H); 3.1(t, 2H); 4.9(t, 2H); 6.9–7.8(m, 8H); 12.8(s, 1H). |
| 150 | (250MHz, DMSOd6): 1.7–2.50(m, 6H); 2.2(s, 6H); 3.75(m, 1H); 4.25(m, 1H); 6.5(m, 1H); 7.2–8.05(m, 9H); 12.9(s, 1H). |
| 151 | (200MHz, DMSOd6): 3.7(s, 3H); 5.5(s, 2H); 7.2–7.9 (m, 10H); 12.9(s, 1H). |
| 152 | (200MHz, DMSOd6): 5.3(s, 2H); 7.1–7.9(m, 10H); 13.1(s, 2H). |
| 153 | (200MHz, DMSOd6): 1.46(s, 9H); 3.75(s, 6H); 3.90 (2s, 6H); 5.40(s, 2H); 6.38(s, 2H); 6.97(s, 1H); 7.00 (s, 1H); 7.20(d, 1H); 7.60(d, 1H); 7.80(s, 1H); 12.80(s, 1H). |
| 154 | (200MHz, DMSOd6): 1.10(t, 6H); 1.40(t, 3H); 1.50(s, 9H); 3.80(s, 3H); 4.00(q, 4H); 4.16(q, 2H); 5.40(s, 2H); 6.30 (s, 2H); 6.99(s, 1H); 7.01(s, 1H); 7.20(d, 1H); 7.60(d, 1H); 7.80(s, 1H); 12.60(s, 1H). |
| 155 | (200MHz, DMSOd6): 1.20(t, 6H); 1.40(t, 3H); 3.82(s, 3H); 4.00(q, 4H); 4.10(q, 2H); 5.40(s, 2H); 6.20(s, 2H); 7.00(s, 1H); 7.05(s, 1H); 7.20(d, 1H); 7.60(d, 1H); 7.75(s, 1H); 12.70(s, 1H). |
| 156 | (200MHz, DMSOd6): 3.80(s, 6H); 3.92(s, 3H); 5.50(s, 2H); 6.40(s, 2H); 6.50(d, 1H); 7.00(m, 3H); 7.70(s, 1H); 11.20(s, 1H); 12.80(s, 1H). |
| 157 | (200MHz, DMSOd6): 3.70(s, 6H); 3.80(s, 3H); 3.82(s, 3H); 5.18(s, 2H); 6.37(s, 2H); 6.90(s, 1H); 7.00(s, 1H); 7.10(s, 1H); 7.50(m, 6H); 11.60(s, 1H); 12.80(s, 1H). |
| 158 | (200MHz, DMSOd6): 3.80(s, 6H); 3.84(s, 3H); 6.40(s, 2H); 7.02(s, 1H); 7.40(t, 1H); 7.80(s, 1H); 8.40(2d, 2H); 11.50(s, 1H); 12.80(s, 1H). |
| 159 | (200MHz, DMSOd6): 1.04(t, 6H); 1.25(t, 3H); 2.40(q, 4H); 2.70(q, 2H); 7.00(s, 1H); 7.08(m, 2H); 7.30(t, 1H); 7.55(d, 1H); 7.70(m, 2H); 11.50(s, 1H); 12.60(s, 1H). |
| 160 | (200MHz, DMSOd6): 2.12(s, 6H); 7.05–7.70(m, 9H); 11.96(s, 1H). |
| 161 | (200MHz, DMSOd6): 2.08(s, 6H); 2.27(s, 3H); 3.77(s, 3H); 11.83(s, 1H). |
| 162 | (200MHz, DMSOd6): 2.07(s, 6H); 2.28(s, 3H); 6.92–7.77 (m, 8H); 12.18(s, 1H). |

TABLE IX-continued

| EXAMPLES | δ(ppm) |
|---|---|
| 163 | (200MHz, DMSOd6): 7.1–8.0(m, 10H); 9.0(s, 2H); 11.9(s, 1H). |
| 164 | (200MHz, DMSOd6): 2.48(s, 3H); 7.09–7.71(m, 10H); 11.94(s, 1H); 12.79(s, 1H). |
| 165 | (200MHz, DMSOd6): 7.05–7.88(m, 10H); 11.93(s, 1H); 12.82(s, 1H). |
| 166 | (200MHz, DMSOd6): 1.29–1.82(m, 10H); 2.5(m, 1H); 3.25(m, 1H); 3.50(m, 1H); 4.80(m, 1H); 6.86–7.83(m, 9H); 9.29(m, 2H); 12.50(m, 1H). |
| 167 | (200MHz, DMSOd6): 2.35(s, 3H); 2.49(s, 3H); 7.05–7.69 (m, 9H); 11.91(s, 1H); 12.67(s, 1H). |
| 168 | (200MHz, DMSOd6): 2.078(s, 6H); 2.27(s, 3H); 6.93–8.05 (m, 8H); 13.04(s, 1H). |

We claim:

1. A 2-Acylaminothiazole of formula

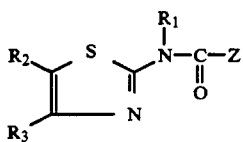

in which $R_1$ represents H, ($C_1$ to $C_4$) alkyl or phenyl($C_1$-$C_3$)alkyl; aminoalkyl —$Z_1$-$NR_4R_5$, in which $Z_1$ represents a ($C_2$ to $C_4$) alkylene and $R_4$ and $R_5$ independently represent H or ($C_1$ to $C_4$) alkyl, or form with N a saturated heterocycle and represent morpholino, pyrrolidinyl piperidino, piperazinyl or 4-($C_1$-$C_3$)alkylpiperazinyl; carboxyalkyl —$Z_2$—$COOR_6$, in which $Z_2$ represents ($C_1$ to $C_4$) alkylene and $R_6$ represents H or ($C_1$ to $C_6$) alkyl; ($C_2$ to $C_5$) cyanoalkyl; carbamoylalkyl —$Z_3$—$CONR_7R_8$, in which $Z_3$ represents ($C_1$ to $C_4$) alkylene and $R_7$ and $R_8$ independently represent H or ($C_1$ to $C_4$) alkyl or, with N, represent a heterocycle selected from $NR_4R_5$; ($C_2$ to $C_6$) hydroxyalkyl and ($C_2$ to $C_{10}$) alkoxyalkyl;

$R_2$ represents H or ($C_1$ to $C_4$) alkyl;

$R_3$ represents ($C_5$ to $C_8$) cycloalkyl, optionally substituted by one or more ($C_1$ to $C_4$) alkyl; an aromatic group, selected from phenyl, optionally carrying one or more substituents chosen from halogen, ($C_1$-$C_6$) alkyl, ($C_1$-$C_3$) alkoxy and ($C_1$-$C_3$) thioalkoxy, nitro, trifluoromethyl and a heterocycle comprising at least one heteroatom chosen from O, S and N, and $R_3$ then represents furyl, thienyl, pyrroly, pyrazolyl, imidazolyl, pyridyl, pyrazinyl, oxazolyl or thiazolyl, optionally substituted by ($C_1$ to $C_3$) alkyl or halogen, or $R_2$ and $R_3$ considered together represent the group

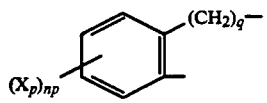

fixed by the carbon of the phenyl in position 4 of the thiazolyl and in which q is 1 to 4, and $X_p$ represents the optional substituents chosen from halogen, ($C_1$-$C_3$) alkyl, ($C_1$-$C_3$) alkoxy, nitro and trifluoromethyl and np represents 0 to 3, and Z represents a heterocycle comprising one or more hetero-atoms chosen from O, S and N, fused with an aromatic ring which may comprise a hetero-atom and which aromatic ring may be substituted by one or more groups chosen from halogen, ($C_1$-$C_3$) alkyl, ($C_1$-$C_3$) alkoxy, benzyloxy, nitro, amino and trifluoromethyl, and which heterocycle is unsubstituted or substituted on the N atom by $C_1$-$C_4$ alkyl; $C_1$-$C_6$ hydroxyalkyl; optionally cyclised ($C_2$-$C_{10}$) alkoxyalkyl, aminoalkyl —$Z_4$—$NR_{10}R_{11}$ in which $Z_4$ represents ($C_2$-$C_4$) alkylene and $R_{10}$ and $R_{11}$ independently represent H or ($C_1$-$C_4$) alkyl, or $NR_{10}R_{11}$ represents with N a saturated heterocyclic group selected from morpholino, pyrrolidinyl, piperidino, piperazinyl or 4-($C_1$-$C_3$)-alkylpiperazinyl; carboxyalkyl —$Z_5$—$COOR_{12}$ in which $Z_5$ represents ($C_1$-$C_4$) alkylene and $R_{12}$ is H, benzyl or ($C_1$-$C_6$) alkyl; carbamoylalkyl —$Z_6$-$CONR_{13}R_{14}$, in which $Z_6$ represents ($C_1$-$C_4$) alkylene and $R_{13}$ and $R_{14}$ independently represent H or ($C_1$-$C_6$) alkyl or form, with N, a saturated heterocycle selected from $NR_{10}R_{11}$; acyl —$COR_{15}$, where $R_{15}$ represents ($C_1$-$C_4$) alkyl or phenyl; or alkoxycarbonyl —$COOR_{16}$, with $R_{16}$ being tert-butyl or benzyl; as well as the addition salts of the compounds of formula I with inorganic or organic acids and bases.

2. A Compound according to claim 1, of formula I in which Z represents benzothienyl, benzofuranyl, benzoxazolyl, benzimidazolyl, benzothiazolyl, quinolyl, isoquinolyl, quinoxalinyl, quinazolinyl, cinnolinyl and [2,3-c] or [3,2-c]thienopyridyl, isoindolyl, isoindolinyl, optionally substituted indolyl or indolinyl and the indolyl and indolinyl groups being optionally substituted on nitrogen.

3. A Compound according to claim 1, of formula I, in which $R_2$ represents H, $R_1$ represents H, ($C_1$-$C_4$) alkyl or —$Z_1$—$NR_4R_5$, with $Z_1$, $R_4$ and $R_5$ having the same meanings as in claim 1, $R_3$ represents an at least ortho-substituted phenyl and Z represents an indolyl group which is unsubstituted or substituted on the nitrogen by ($C_1$-$C_4$) alkyl, ($C_2$-$C_6$) hydroxyalkyl; ($C_2$-$C_{10}$) alkoxyalkyl; aminoalkyl —$Z_4$—$NR_{10}$—$R_{11}$ in which $Z_4$ represents ($C_2$-$C_4$) alkylene and $R_{10}$ and $R_{11}$ independently represent H or ($C_1$-$C_4$) alkyl, or $NR_{10}R_{11}$ represents with N a saturated heterocyclic group selected from morpholino, pyrrolidinyl, piperidino, piperazinyl or 4-($C_1$-$C_3$) alkylpiperazinyl; carboxyalkyl —$Z_5$—$COOR_{12}$ in which $Z_5$ represents ($C_1$-$C_4$) alkylene and $R_{12}$ is H, benzyl or ($C_1$-$C_6$) alkyl; carbamoylalkyl —$Z_6$—$CONR_{13}R_{14}$, in which $Z_6$ represents ($C_1$-$C_4$) alkylene and $R_{13}$ and $R_{14}$ independently represent H or ($C_1$-$C_6$) alkyl or form, with N, a saturated heterocycle selected from $NR_{10}R_{11}$; acyl —$COR_{15}$, where $R_{15}$ represents ($C_1$-$C_4$) alkyl or phenyl; or alkoxycarbonyl —$COOR_{16}$, with $R_{16}$ being tert-butyl or benzyl; and their salts.

4. N-[4(2,4,6-Trimethylphenyl)-2-thiazolyl]-indole-2-carboxamide and its derivatives substituted on the indole nitrogen by $CH_3$, $CH_2COOH$, $CH_2COOCH_3$ or $(CH_2)_2N(CH_3)_2$, and their pharmaceutically acceptable salts.

5. N-[4(2,4,6-Trimethoxyphenyl)-2-thiazolyl]indole-2-carboxamide and its derivatives substituted on the indole nitrogen by CH$_3$,k CH$_2$COOH, CH$_2$COOCH$_3$ or (CH$_2$)$_2$N(CH$_3$)$_2$, and their pharmaceutically acceptable salts.

6. N-[4(2,4,6-Dimethylphenyl)-2-thiazolyl]-indole-2-carboxamide and its derivatives substituted on the indole nitrogen by CH$_2$COOH and CH$_2$COOCH$_3$, and their pharmaceutically acceptable salts.

7. N-[4(2,4,6-Dimethoxyphenyl)-2-thiazolyl]-indole-2-carboxamide and its derivatives substituted on the indole nitrogen by CH$_2$COOH and CH$_2$COOH and CH$_2$COOCH$_3$, and their pharmaceutically acceptable salts.

8. N-[4(2,4,6-Dichlorophenyl)-2-thiazolyl]-indole-2-carboxamide and its derivatives substituted on the nitrogen by CH$_2$COOH and (CH$_2$)$_2$N(CH$_3$)$_2$, and their pharmaceutically acceptable salts.

9. N-[4-(2-Methylphenyl)-2-thiazolyl]-indole-2-carboxamide, N-[4-(2-methoxyphenyl)-2-thiazolyl]-indole-2-carboxamide, N-[4-(2-chlorophenyl)-2-thiazolyl]-indole-2-carboxamide and their derivatives substituted on the nitrogen by CH$_2$COOH and also their pharamaceutically acceptable salts.

10. N-[4-(4-Methylphenyl)-2-thiazolyl]-indole-2-carboxamide and N-[4-(4-methoxyphenyl)-2-thiazolyl]indole-2-carboxamide and their pharmaceutically acceptable salts.

11. N-[4-(2,4,6-trimethoxyphenyl)-2-thiazolyl]benzofuran-2-carboxamide and its pharmaceutically acceptable salts.

12. A 2-acylaminothiazole of formula

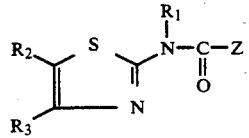

in which
R$_1$ represents H, (C$_1$-C$_4$) alkyl or phenyl(C$_1$-C$_3$)alkyl;
R$_2$ represents H or (C$_1$-C$_4$)alkyl;
R$_3$ represents (C$_5$-C$_8$)cycloalkyl, optionally substituted by one or more (C$_1$-C$_3$) alkyl; an aromatic group optionally carrying one or more substituents chosen from halogen, (C$_1$-C$_3$)alkyl, (C$_1$-C$_3$) alkoxy and (C$_1$-C$_3$)thioalkoxy, nitro, trifluoromethyl, said aromatic group being selected from phenyl and a heterocyclic group furyl, thienyl, pyrrolyl and pyridyl, or R$_2$ and R$_3$ considered together represent the group

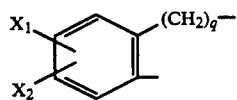

fixed by the carbon of the phenyl in position 4 of the thiazolyl and in which X$_1$ and X$_2$ each represents hydrogen, halogen, (C$_1$-C$_3$)alkyl, (C$_1$-C$_3$)alkoxy, nitro or trifluoromethyl, and q is 1 to 4, and Z represents a nitrogen comprising heterocycle fused with a phenyl ring selected from indolinyl, isoindolinyl, indolyl, isoindolyl, quinolyl and isoquinolyl, optionally substituted on the phenyl ring by one or more groups selected from halogen, (C$_1$-C$_3$)alkyl, (C$_1$-C$_3$)alkoxy and thioalkoxy or the addition salt of this compound with a pharmaceutically acceptable acid.

13. A compound according to claim 12 of formula I in which Z represents a group selected from optionally substituted indolyl and quinolyl.

14. A 2-acylaminothiazole of formula

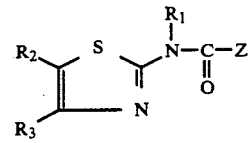

in which
R$_1$ represents H, (C$_1$-C$_4$)alkyl or phenyl(C$_1$-C$_3$)alkyl; aminoalkyl —Z$_1$—NR$_4$R$_5$, in which Z$_1$ represents a (C$_2$-C$_4$)alkylene and R$_4$ and R$_5$ independently represent H or (C$_1$-C$_4$)alkyl, or form with N a saturated heterocycle morpholino, pyrrolidinyl, piperidino, piperazinyl or 4-(C$_1$-C$_3$)alkylpiperazinyl; carboxyalkyl —Z$_2$—COOR$_6$, in which Z$_2$ represents (C$_1$-C$_4$)alkylene and R$_6$ represents H or (C$_1$-C$_6$)-alkyl; (C$_2$-C$_5$)cyanoalkyl; carbamoylalkyl —Z$_3$-CONR$_7$R$_8$, in which Z$_3$ represents (C$_1$-C$_4$)alkylene and R$_7$ and R$_8$ independently represent H or (C$_1$-C$_4$)alkyl; (C$_2$-C$_6$)hydroxyalkyl or (C$_2$-C$_{10}$)alkoxyalkyl; R$_2$ represents H or (C$_1$ to C$_4$)alkyl; R$_3$ represents (C$_5$-C$_8$)cycloalkyl, optionally substituted by one or more (C$_1$-C$_3$)alkyl; and aromatic group, optionally carrying one or more substituents selected from halogen, (C$_1$-C$_3$)alkyl, (C$_1$-C$_3$)alkoxy and (C$_1$-C$_3$)thioalkoxy, nitro and trifluoromethyl, said aromatic group being selected from phenyl furyl, thienyl, pyrrolyl and pyridyl, or R$_2$ and R$_3$ considered together represent the group

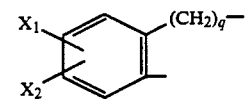

fixed by the carbon of the phenyl in position 4 of the thiazolyl and in which X$_1$ and X$_2$ each represents hydrogen, halogen, (C$_1$-C$_3$-alkyl, (C$_1$-C$_3$)alkoxy, nitro or trifluoromethyl, and q is 1to 4, and
Z represents an indolyl group of formula

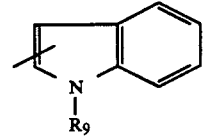

in which R$_9$ represents (C$_2$-C$_6$)hydroxyalkyl; acyclic or cyclic (C$_2$-C$_{10}$)alkoxyalkyl; aminoalkyl —Z$_4$—NR$_{10}$R$_{11}$ in which Z$_4$ represents (C$_2$-C$_4$)alkylene and R$_{10}$ and R$_{11}$ independently represent H or (C$_1$-C$_4$)alkyl, or represent with N a saturated heterocyclic group selected from morpholino, pyrrolidinyl, piperidino, piperazinyl and 4-(C$_1$-C$_3$)alkylpiperazinyl; carboxyalkyl —Z$_5$—COOR$_{12}$ in which Z$_5$ represents (C$_1$-C$_4$)alkylene and R$_{12}$ is H or (C$_1$-C$_6$)alkyl; cyano(C$_1$-C$_4$)alkyl; carbamoylalkyl Z$_6$-CONR$_{13}$R$_{14}$, in which Z$_6$ represents (C$_1$-C$_4$)alkylene and R$_{13}$ and R$_{14}$ independently represent H or (C$_1$-C$_4$)alkyl or form, with N, a saturated heterocycle; acyl —COR$_{15}$, where R$_{15}$ represents (C$_1$-C$_4$)alkyl or phenyl; or alkoxycarbonyl —COOR$_{16}$, with R$_{16}$ being tert-butyl or benzyl; and in which the phenyl ring may be substituted with one or more groups selected from (C$_1$-C$_3$)alkyl, (C$_1$-C$_3$)alkoxy, halogen, trifluoromethyl, and nitro, or the pharmaceutically acceptable acid addition salt of this compound.

15. A pharmaceutical composition for the prevention or treatment of disorders requiring cholecystokinin or gastrin antagonists, characterized in that it comprises a pharmaceutically effective amount of at least one compound according to claim 1, in combination with at least one excipient.

* * * * *